United States Patent
Dumesic et al.

(10) Patent No.: US 9,617,234 B1
(45) Date of Patent: Apr. 11, 2017

(54) METHOD TO PRODUCE FURANDICARBOXYLIC ACID (FDCA) FROM 5-HYDROXYMETHYLFURFURAL (HMF)

(71) Applicant: Wisconsin Alumni Research Foundation, Madison, WI (US)

(72) Inventors: James A. Dumesic, Verona, WI (US); Ali Hussain Motagamwala, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/974,468

(22) Filed: Dec. 18, 2015

(51) Int. Cl.
C07D 307/02 (2006.01)
C07D 307/68 (2006.01)

(52) U.S. Cl.
CPC .................................. *C07D 307/68* (2013.01)

(58) Field of Classification Search
CPC ........................... C07D 307/46; C07D 307/68
USPC ....................................................... 549/485
See application file for complete search history.

(56) References Cited

U.S. PATENT DOCUMENTS

2012/0271060 A1* 10/2012 Munoz de Diego ... C07D 307/68 549/485
2014/0295508 A1* 10/2014 Yoshikuni ............ C07D 307/68 435/137

OTHER PUBLICATIONS

Reichardt, Solvents and Solvent Effects in Organic Chemistry, 3rd ed., 2003, p. 471-507.*

Alamillo et al., The selective hydrogenation of biomass-derived 5-hydroxymethylfurfural using heterogeneous catalysts. *Green Chemistry*, 2012. 14(5): p. 1413-1419.

Alonso et al., Catalytic conversion of biomass to biofuels, *Green Chemistry*, 2010, 12, 1493-1513.

Amarasekara et al., Mechanism of the dehydration of D-fructose to 5-hydroxymethylfurfural in dimethyl sulfoxide at 150° C.: an NMR study, *Carbohydrate Research*, 2008, 343, 3021-3024.

Antal Jr, et al., Mechanism of formation of 5-(hydroxymethyl)-1-furaldehyde from D-fructose and sucrose, *Carbohydrate Research*, 1990, 199, 91-109.

Binder et al., Simple Chemical Transformation of Lignocellulosic Biomass into Furans for Fuels and Chemicals, *Journal of the American Chemical Society*, 2009, 131, 1979-1985.

Bozell et al., Technology development for the production of biobased products from biorefinery carbohydrates—the US Department of Energy's "Top 10" revisited, *Green Chemistry*, 2010, 12, 539-554.

(Continued)

*Primary Examiner* — T. Victor Oh
*Assistant Examiner* — Taylor V Oh
(74) *Attorney, Agent, or Firm* — Joseph T. Leone, Esq.; DeWitt Ross & Stevens S.C.

(57) ABSTRACT

A process to produce furandicarboxylic acid (FDCA). The process includes the steps of reacting a C6 sugar-containing reactant in a reaction solution comprising a first organic solvent selected from the group consisting of beta-, gamma-, and delta-lactones, hydrofurans, hydropyrans, and combinations thereof, in the presence of an acid catalyst for a time and under conditions wherein at least a portion of the C6 sugar present in the reactant is converted to 5-(hydroxymethyl)furfural (HMF); oxidizing the HMF into FDCA with or without separating the HMF from the reaction solution; and extracting the FDCA by adding an aprotic organic solvent having a dipole moment of about 1.0 D or less to the reaction solution.

25 Claims, 16 Drawing Sheets

(56) References Cited

OTHER PUBLICATIONS

Cass, O.W., Chemical Intermediates From Furfural, *Industrial & Engineering Chemistry*, 1948, 40, 216-219.
Chheda et al., Production of 5-hydroxymethylfurfual and furfural by dehydration of biomass-derived mono- and poly-saccharides, *Green Chemistry*, 2007, 9, 342-350.
Crisci et al., Acid-Functionalized SBA-15-Type Silica Catalysts for Carbohydrate Dehydration, *Acs Catal*, 2011, 1, 719-728.
Davis et al., Oxidation of 5-hydroxymethylfurfural over supported Pt, Pd and Au catalysts, *Catal Today*, 2011, 160, 55-60.
Davis et al., On the mechanism of selective oxidation of 5-hydroxymethylfurfural to 2,5-furandicarboxylic acid over supported Pt and Au catalysts, *Green Chemistry*, 2012, 14, 143-147.
Dutta et al., Direct conversion of cellulose and lignocellulosic biomass into chemicals and biofuel with metal chloride catalysts. *Journal of Catalysis*, 2012. 288: p. 8-15.
Garcia-Suarez et al., Versatile dual hydrogenation-oxidation nanocatalysts for the aqueous transformation of biomas-derived platform molecules, *Green Chemistry*, 2012, 14, 1434-1439.
Guan et al., The mechanism of glucose conversion to 5-hydroxymenthylfurfual catalyzed by metal chlorides in ionic liquid: A theoretical study, *Comput Theor Chem*, 2011, 963, 453-462.
Huang et al., Integrating enzymatic and acid catalysis to convert glucose into 5-hydroxymethylfurfural, *Chem Commun*, 2010, 46, 1115-1117.
Manzer, L.E., Catalytic synthesis of α-methylene-γ-valerolactone: a biomass-derived arcylic monomer, *Appl Catal a-Gen*, 2004, 272, 249-256.
Moliner et al., Tin-containing zeolites are highly active catalysts for the isomerization of glucose in water, *P Natl Acad Sci USA*, 2010, 107, 6164-6168.
Moreau et al., Dehydration of fructose and sucrose into 5-hydroxymenthylfurfural in the presence of 1-H-3-methyl imidazolium chloride acting both as a solvent and catalyst, *Journal of Molecular Catalysis A: Chemical*, 2006, 253, 165-169.
Nikolla et al., "One-Pot" Synthesis of 5-(Hydroxymethyl)furfural from Carbohydrates using Tin-Beta Zeolite, *Acs Catal*, 2011, 1, 408-410.
Osmundsen et al., Tin-containing silicates: structure-activity relations, *Proceedings of the Royal Society a-Math Phy*, 2012, 468, 2000-2016.
Pagan-Torres et al., Production of 5-Hydroxymethylfurfural from Glucose Using a Combination of Lewis and Bronsted Acid Catalysts in Water in a Biphasic Reactor with an Alkylphenol Solvent, *Acs Catal*, 2012, 2, 930-934.
Pilath et al., Glucose Reversion Reaction Kinetics, *J Agr Food Chem*, 2010, 58, 6131-6140.
Robyt, J.F., *Essentials of carbohydrate chemistry*, Springer Pub. Co., New York, 1998 (Book).
Román-Leshkov et al., Phase Modifiers Promote Efficient Production of Hydroxymethylfurfural from Fructose, *Science*, 2006, 312, 1933-1937.
Román-Leshkov et al., Production of dimethylfuran for liquid fuels from biomass-derived carbohydrates, *Nature*, 2007, 447, 982-U985.
Román-Leshkov et al., Solvent Effects on Fructose Dehydration to 5-Hyroxymethylfurfural in Biphasic Systems Saturated with Inorganic Salts, *Topics in Catalysis*, 2009, 52, 297-303.
Serrano-Ruiz et al., Transformations of biomass-derived platform molecules: from high added-value chemicals to fuels via aqueous-phase processing, *Chem Soc Rev*, 2011, 40, 5266-5281.
Shah et al., Direct hydrothermal synthesis of mesoporous Sn-SBA-15 materials under weak acidic conditions, *Micropor Mesopor Mat*, 2007, 100, 210-226.
Shimizu et al., Enhanced production of hydroxymethylfurfural from fructose with solid acid catalysts by simple water removal methods, *Catalysis Communications*, 2009, 10, 1849-1853.
Takagaki et al., a one-pot reaction for biorefinery: combination of solid acid and base catalysts for direct production of 5-hydroxymethylfurfural from saccharides, *Chem Commun*, 2009, 6276-6278.
Tucker, M.H., Selective Production of Value Added Chemicals From Fructose Using Heterogeneous Catalysis, *Chemical & Biological Engineering*. 2011, University of Wisconsin-Madison: Madison.
Ugurchieva et al., Synthesis of (±)-4-alkanolides from pent-4-enoic acid, *Russ Chem B+*, 2008, 57, 657-659.
Werpy et al., Top Value Added Chemicals from Biomass, vol. 1—Results of Screening for Potential Candidates from Sugars and Synthesis Gas, U.S. Department of Energy, 2004.
Wettstein et al., Production of levulinic acid and gamma-valerolactone (GVL) from cellulose using GVL as a solvent in biphasic systems, *Energy & Environmental Science*, 2012, 5, 8199-8203.
Wyman et al., Coordinated development of leading biomass pretreatment technologies. *Bioresource Technology*, 2005. 96(18): p. 1959-1966.
Yang et al., Conversion of carbohydrates and lignocellulosic biomass into 5- hydroxymethylfurfural using AlCl3 center dot 6H(2)O catalyst in a biphasic solvent system. *Green Chemistry*, 2012. 14(2): p. 509-513.
Yong et al., Efficient Catalytic System for the Selective Production of 5-Hydroxymethylfurfural from Glucose and Fructose, *Angewandte Chemie International Edition*, 2008, 47, 9345-9348.
Zakrzewska et al., Ionic Liquid-Mediated Formation of 5-Hydroxymethylfurfural—A Promising Biomass-Derived Building Block, *Chem Rev*, 2011, 111, 397-417.
Zhang et al., Optimal design and operation of SMB bioreactor: production of high fructose syrup by isomerization of glucose, *Biochemical Engineering Journal*, 2004, 21, 111-121.
Zhao et al., Metal Chlorides in Ionic Liquid Solvents Convert Sugars to 5-Hydroxymethylfurfural, *Science*, 2007, 316, 1597-1600.
Zhou et al., Solid acid catalysis of tandem isomerization-lactonization of olefinic acids, *Applied Catalysis A: General*, 2007, 333, 238-244.
Zope et al., Influence of Reaction Conditions on Diacid Formation Druing Au-Catalyzed Oxidation of Glycerol and Hydroxymethylfurfural, *Topics in Catalysis*, 2012, 55, 24-32.

* cited by examiner

Advantages:
- HMF obtained in high yields
- GVL can be obtained from biomass
- Low Toxicity of GVL
- No mixing problems
- No need of phase separation
- Homogeneous/heterogneous catalysts can be used Solvent: mixture of water and lactone or tetrahydropyran;
Brønsted Acid: Amberlyst 70 (Amb70)
Lewis Acid: Sn-SBA-15 (Sn$^{+4}$/Silica), SnO$_2$/Al-β or Sn-β

Advantages:
- Solvents can be obtained from biomass
- Low Toxicity
- No mixing problems
- No need of phase separation
- Solid catalysts can be easily removed from reaction

METHOD TO PRODUCE FURANDICARBOXYLIC ACID (FDCA) FROM 5-HYDROXYMETHYLFURFURAL (HMF)

FEDERAL FUNDING STATEMENT

This invention was made with government support under DE-FC02-07ER64494 awarded by the US Department of Energy. The government has certain rights in the invention.

BACKGROUND

The conversion of renewable biomass resources into chemicals and fuels traditionally obtained from petroleum is strategically important to improve the sustainability of the chemical industry. Lignocellulosic biomass is the non-edible portion of biomass, and extensive research has been carried out in its conversion into platform molecules. The platform molecule 5-hydroxymethylfurfural (HMF), produced from the Brønsted acid-catalyzed dehydration of $C_6$ sugars (hexoses), is considered to be one of the top value-added chemicals.[1, 2] Mechanistic studies have shown that HMF is formed from the dehydration of the hexoses in the furanose form (5 member ring).[2-4] Although glucose is the most abundant and least expensive hexose, it presents low amounts of furanose isomer in solution (1% in water [5]), and its dehydration into HMF thus takes place with low selectivity.[6] In contrast, fructose, which presents 21.5% of the furanose form in aqueous solution,[5] can be dehydrated to HMF in higher yields using monophasic or biphasic solvent systems, and using homogeneous and heterogeneous Brønsted acids.[7-13] Dumesic and co-workers[14, 15] employed a biphasic system consisting of an aqueous layer saturated with NaCl and containing fructose and HCl or $H_2SO_4$ as catalysts, in combination with an extracting organic layer to protect HMF from degradation reactions. Several alcohols, ketones and ethers were used as extracting organic layers, and yields for HMF as high as 70% were observed.[14, 15] In monophasic solvent systems using dimethyl sulfoxide or ionic liquids as solvents, HMF can be obtained with yields higher than 90%.[7, 11, 16] However, the separation and purification of HMF from these solvents are complicated.

While glucose can be obtained from cellulose by hydrolysis with yields of 98-100%, isomerization of glucose to fructose is economically limited to 42%, [17] requiring additional and expensive separation steps. As a consequence, the final market price of fructose is significantly higher than that of glucose. In order to obtain HMF in high yields from glucose, recent studies have aimed to use one-pot isomerization reactions to produce fructose by using a Lewis acid or Lewis base, followed by Brønsted acid-catalyzed dehydration of fructose to HMF. See Reaction Scheme 1 and FIG. 1. Reaction Scheme 1 depicts the conversion of glucose to HMF by a combined isomerization/dehydration reaction pathway. FIG. 1 is a very abbreviated reaction scheme showing how furfural and HMF can be derived from a biomass feedstock.

Zhao et al.[18] first reported HMF yields of 68-70% from glucose in the ionic liquid 1-ethyl-3-methyl-imidazolium chloride using $CrCl_2$ as the Lewis acid catalyst. In subsequent studies with ionic liquids, HMF was produced from glucose with yields higher than 90%.[19] However, ionic liquids are not suitable for large scale applications due to their high cost and deactivation by small amounts of water. [7] Binder, et al.[12] reported that a system using dimethylacetamide (DMA), NaBr and $CrCl_2$ resulted in HMF yields of 81%, being as effective as ionic liquid systems. Other authors have explored biphasic systems. Huang et al.[20] reported a 63% HMF yield in a biphasic reactor system with a two-step process involving the isomerization of glucose to fructose in the presence of glucose isomerase and borate ions, followed by the HCl-catalyzed dehydration of fructose to HMF. Dumesic and co-workers [6] reported 62% yield of HMF from glucose using a biphasic reactor consisting of $AlCl_3.6H_2O$ and HCl as catalysts in water saturated with NaCl, in contact with sec-butylphenol. Abu-Omar et al. reported an HMF yield of 61% from glucose using $AlCl_3.6H_2O$ as the catalyst in a biphasic system where THF was used as the extracting solvent [43, 44]. In all of these systems, the main goal was to maximize HMF yield, while the upgrading and purification of HMF and the sustainability of the process remained as secondary problems. For example, reutilization of homogeneous catalysts can be an issue, and these catalysts lead to corrosions problems that require expensive materials of construction. Moreover, the replacement of these homogeneous catalysts with heterogeneous catalysts is not possible in the presence of salts, due to exchange of protons on the catalyst with cations in solution, leading to deactivation of the heterogeneous catalyst.

Recent studies have shown that hydrotalcites [28] and tin containing zeolites and silicas [29] are active for glucose isomerization to fructose. Using a combination of Sn-β and HCl in a biphasic system, Nikolla et al. [30] obtained HMF yields of 57% at 79% conversion of glucose. No tin leaching was observed. Takagaki, et al. [28] reported HMF yields of 42% at 73% conversion in a two-step process by combining the solid Brønsted acid catalyst, Amberlyst-70 (Amb-70), and a solid base catalyst, hydrotalcite, in N,N-dimethylformamide.

HMF is an important chemical intermediate for a host of downstream reactions. The main reaction pathways for the production of chemicals from HMF are oxidation and hydrogenation. See FIG. 2 for a summary of exemplary reactions that can be conducted using furfural or HMF as the starting material. Hydrogenation, for example, can lead to 2,5-dihydroxymethylfuran (DHMF) or 2,5-dihydroxymethyltetrahydrofuran (DHMTHF) (not shown in FIG. 2). Both compounds are important solvents and monomers for commercially produced polymers [41]. Additionally there has been much commercial interest in converting HMF to 2,5-furandicarboxylic acid (FDCA). FDCA can be used as a monomer or co-monomer to make fiber and packaging Reaction Scheme 1

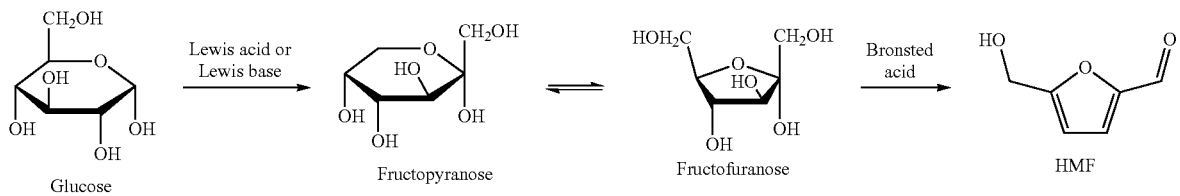

polyesters that compete with polyethylene terephthalate (PET). PET is a commodity polymer that ranks third in world-wide production volume, trailing only polyethylene and polypropylene. World-wide PET production was 49 million tons in 2009.[37]

Importantly, however, separating HMF from organic solvents is extremely difficult. Separating HMF from an organic solvent via distillation requires using high temperatures and/or low pressures, which can lead to degradation of HMF. Also, the high cost of separation and product losses associated with the separation process reduce the economic potential of the overall HMF process. Moreover, HMF is proposed to be a platform chemical which would be upgraded to other value-added chemicals such as 2,5-dimethylfuran (DMF), 5-hydroxymethyl-2-furancarboxylic acid (HMFCA), 2,5-diformylfuran (DFF) and 2,5-furandicarboxylic acid (FDCA). Thus, a process which integrates the upgrading of HMF along with the ease of separation of the final product from the reaction mixture is highly desirable.

The focus of the research to date on HMF production has been on optimizing yields via the judicious selection of solvents and catalysts. But there has been very little research on the feasibility and economics of separating the HMF product from the solvent and catalysts used in the production process. Similarly, there has been very little research on how to integrate the glucose-to-HMF dehydration reaction to downstream reactions to upgrade the HMF into value-added chemicals. In the literature examples mentioned above, intricate separation steps are required to recover the catalysts and the solvents. Economically speaking, the catalysts are sufficiently expensive that they must be recovered to make the processes financially viable. Even if heterogeneous catalysts are used (thus rendering recovery very simple), separating HMF from a high boiling point solvent quickly and economically is not so straightforward. Distillation at high temperatures risks polymerization of the HMF; vacuum distillation increases the cost of the purification.

One of the main drawbacks of the biphasic systems reported by date are that they rely on using salts to drive separation of the two phases and to increase the partition of the HMF into the organic phase. The use of salts in the aqueous phase complicates the use of solid catalysts because they are not long-lasting in the aqueous phase (leaching, collapse) and the acid sites are exchanged by the cation present in the salt, leading to the formation of homogeneous mineral acids. These mineral acids need to be removed from the HMF before further upgrading reactions can be conducted.

Thus, for the economic viability and environmental sustainability of the HMF production process, there is a long-felt and unmet need to produce value-added chemicals from HMF in a process that greatly simplifies or eliminates entirely the need to separate the HMF from the organic solvent in which it is produced.

SUMMARY OF THE INVENTION

Disclosed herein is a process to convert HMF to FDCA with or without separating the HMF from an organic solvent. In the preferred route, the HMF used in the process is obtained from the dehydration of biomass-derived sugars in a lactone solvent, preferably gamma-valerolactone (GVL). In the preferred version of the process, HMF is oxidized in situ with an oxidizing agent such as molecular oxygen over a supported metal catalyst to FDCA. FDCA is then easily extracted from the reaction mixture by adding a relatively inexpensive aromatic solvent, such as toluene, to the reaction mixture. Adding an aromatic solvent to the reaction mixture results in a two-phase system in which a first phase is rich in GVL and the aromatic solvent and a second phase is rich in FDCA. Moreover, GVL can be easily separated by distillation from the organic phase owing to the large difference in the boiling point of GVL (207-208° C.) and toluene (111° C.). Similarly, the FDCA product is easily purified or enriched from any residual solvent due to the high boiling point of FDCA (420° C.). FDCA is also easily crystalized and can be purified by that route.

Disclosed is a process to convert the cellulose fraction of biomass to 5-hydroxymethylfurfural (HMF) and its subsequent oxidation to FDCA with or without separating HMF from the reaction mixture. The process comprises of reacting biomass, cellulose, or any other C6 sugar-containing reactant in a monophasic or biphasic reaction solution comprising an oxygen-containing organic solvent, which can be biomass-derived beta-, gamma- and delta-lactones, hydrofurans and hydropyrans; water can be used as a co-solvent. The reaction is conducted in the presence of an acid catalyst for a time and under conditions such that at least a portion of the C6 sugars present in the reactant is converted to HMF.

The process may optionally further comprise adding a saturating amount of salt to the reaction solution, wherein a biphasic reaction solution is formed.

In certain version of the process, the reaction solution is monophasic and comprises the oxygen-containing organic solvent and, if desired, water. The oxygen-containing organic solvent is selected from the group consisting of water-miscible hydrofurans, hydropyrans, and beta-, gamma- and delta-lactones. Gamma-lactones and tetrahydrofuran containing about 10 wt % or less water are preferred.

The acid catalyst may be a Brønsted acid, a Lewis acid or a combination of Brønsted and Lewis acids. The acid catalyst may be homogeneous or a solid acid catalyst.

The method may further comprise oxygenating the HMF in the presence of an oxygenation catalyst to yield furandicarboxylic acid and other oxidation products, such as 5-hydroxymethylfuranoic acid (HFCA) by oxidation of the formyl group, or 2,5-diformylfuran (DFF) by oxidation of the hydroxy group.

Also disclosed herein is a process to produce furandicarboxylic acid (FDCA). The process comprises reacting a C6 sugar-containing reactant in a reaction solution comprising a first organic solvent selected from the group consisting of beta-, gamma-, and delta-lactones, hydrofurans, hydropyrans, and combinations thereof, in the presence of a heterogenous acid catalyst for a time and under conditions wherein at least a portion of the C6 sugar present in the reactant is converted to 5-(hydroxymethyl)furfural (HMF); and oxidizing at least a portion of the HMF formed into FDCA without separating the HMF from the reaction solution.

The first organic solvent is optionally miscible with water. Alternatively, the first organic solvent may optionally dissolve from about 2 wt % to about 25 wt % water. The first organic solvent may be a combination of two or more solvents, wherein at least one of the solvents is miscible with water and at least one of the other solvents is not miscible with water.

The heterogeneous acid catalyst may optionally be a solid acid catalyst selected from the group consisting of solid Brønsted acid catalysts, solid Lewis acid catalysts, and combinations thereof.

In another version of the method, at least a portion of the HMF is oxidixed into FDCA by contacting the HMF with a catalyst in the presence of an oxidizing agent, such as molecular oxygen. The molecular oxygen may be present at a pressure of from about 100 pounds per square inch (psi) to about 1,000 psi (about 6.805 atm to about 68.05 atm). Pressures above and below this range are explicitly within the scope of the disclosed method.

The metal-containing catalyst may include a metal or a combination thereof from the group consisting of ruthenium, rhodium, palladium, silver, osmium, iridium, platinum, gold, mercury, rhenium, and copper. The catalyst may also include the combinations of precious metals and base metals.

In all of the versions of the process disclosed herein, conversion of HMF into FDCA may be carried out in the absence of added base. Additionally, in all of the versions of the process disclosed herein, at least a portion of the FDCA formed may optionally be extracted by adding to the reaction solution a second organic solvent which is an aprotic organic solvent selected from the group consisting of linear, branched or cyclic alkanes; linear, branched or cyclic alkenes; linear, branched or cyclic ketones; linear, branched or cyclic alcohols; aromatic hydrocarbons; and substituted or unsubstituted phenols. In alternative versions of the process, the second organic solvent may optionally also have a dipole moment of about 1.0 D or less. This second organic solvent is also optionally selected from the group consisting of saturated hydrocarbons, halo-substituted saturated hydrocarbons, aromatic hydrocarbons, and halo-substituted aromatic hydrocarbons. Preferred second organic solvents include, but are not limited to, benzene and toluene.

Another permutation of the method comprises reacting the biomass, cellulose or any other C6 sugar-containing reactant derived from biomass in a monophasic reaction solution, followed by creating a biphasic system having an aqueous phase and an organic phase by adding water and hydrocarbon to the monophasic reaction solution, whereby at least a portion of the HMF is extracted into the resulting aqueous phase. Alternatively, the method may further comprise oxygenating the HMF in the presence of an oxygenation catalyst to yield furandicarboxylic acid.

More specifically, disclosed and claimed herein is a process to produce 5-hydroxymethylfurfural (HMF) and its further oxidation to FDCA. The process comprises reacting a C6 sugar-containing reactant in a monophasic reaction solution comprising (i) an organic solvent selected from the group consisting of beta-, gamma-, and delta-lactones, hydrofurans, hydropyrans, and combinations thereof, and (ii) at least about 1 wt % water; in the presence of a heterogeneous acid catalyst for a time and under conditions wherein at least a portion of the substrate present in the reactant is converted to HMF. The HMF so obtained is then oxidized to FDCA without separating HMF from the reaction solution.

The oxygen-containing organic solvent may be miscible with water, or the oxygen-containing organic solvent may be immiscible with water, but capable of dissolving from 2 wt % to 25 wt % water. The oxygen-containing organic solvent may be a combination of two or more solvents, wherein at least one of the solvents is miscible with water and at least one of the other solvents is not miscible with water, wherein the resulting mixture is either miscible with water or capable of dissolving from about 1% water to about 25 wt % water.

The HMF so formed may be oxygenated in the presence of an oxygenation catalyst, for a time and under conditions wherein at least a portion of the HMF is converted to furandicarboxylic acid.

The heterogeneous acid catalyst may be a solid acid catalyst selected from the group consisting of solid Brønsted acid catalysts, solid Lewis acid catalysts, and combinations thereof. For example, the solid acid catalyst may be a heteropolyacid, a mesoporous silica, a zeolite, an acidic material on a thermo-stable support (in which case the thermostable support may be selected from tin oxide, alumina, niobia, zirconia, titania, and carbon, among many other suitable selections), a solid acidic metal oxide, and/or a solid acidic ion exchanger. If a solid ion exchanger is used as the heterogeneous acid catalyst, it is preferred that it comprise cross-linked polystyrene-containing sulfonic acid groups and/or sulfonated tetrafluoroethylene-based fluoropolymer-copolymers.

When the heterogeneous acid catalyst is a solid Brønsted acid catalyst, a solid Lewis acid catalyst, or a combination of the two, the process may again optionally include oxygenating the HMF in the presence of an oxygenation catalyst, for a time and under conditions wherein at least a portion of the HMF is converted to furandicarboxylic acid.

In any and all of the monophasic processes recited above, the monophasic reaction solution may comprise from about 5 wt % to about 25 wt % water, or from about 5 wt % to about 12 wt % water.

The process may further comprise, after reacting the C6 sugar-containing reactant to yield HMF, adding a sufficient quantity of a mixture of water and hydrocarbon to the monophasic reaction solution to create a biphasic system having an organic phase and an aqueous phase, wherein at least a portion of the HMF is extracted into the resulting aqueous phase. Once extracted into the aqueous phase, at least a portion of the HMF may optionally be oxygenated in the presence of an oxygenation catalyst, for a time and under conditions wherein at least a portion of the HMF is converted to furandicarboxylic acid.

Another version of the process is directed to a process to produce 5-hydroxymethylfurfural (HMF). Here, the process comprises reacting a C6 sugar-containing reactant in a biphasic reaction solution comprising (i) an aqueous phase, and (ii) an organic phase comprising a water-immiscible solvent selected from the group consisting of beta-, gamma-, and delta-lactones, hydrofurans, hydropyrans, and combinations thereof; in the presence of an acid catalyst for a time and under conditions wherein at least a portion of the C6 sugar present in the reactant is converted to HMF. The aqueous phase may optionally comprise a saturating amount of a salt.

As noted for the other versions of the process, wherein the acid catalyst may be selected from the group consisting of Brønsted acid catalysts, Lewis acid catalysts, and combinations thereof. The catalyst may be homogeneous or heterogeneous. The organic solvent may have from four (4) carbon atoms to sixteen (16) carbon atoms, or from four (4) carbon atoms to eleven (11) carbon atoms. As noted in prior versions of the process, the process may further comprise oxygenating at least a portion of the HMF in the presence of an oxygenation catalyst, for a time and under conditions wherein at least a portion of the HMF is converted to furandicarboxylic acid.

While glucose is obtained from cellulose in quantitative yield (98-100%), glucose isomerization to fructose is economically limited to roughly 42% [17]. As a consequence, the market price of fructose is often twice as high as the market price of glucose. Thus, the production of HMF from glucose instead of fructose is a more cost-efficient process. Herein is disclosed and claimed an integrated process using solid acid catalysts and biomass-derived solvents, γ-lactones, hydrofurans and hydropyrans for converting glucose to HMF. Optionally, the HMF so formed may be upgrading to FDCA by oxidation.

As described in greater detail below, the sustainability of the biomass conversion process would be improved by the use of biomass-derived solvents, alleviating the need to purchase and transport petroleum-derived solvents to the biomass conversion site. These solvents must operate in the presence of solid catalysts at reaction conditions favorable for glucose and/or fructose dehydration, and optimally they should be compatible with upgrading processes, which typically involve oxidation, hydrogenation, and/or hydrogenolysis reactions (although this is not required).

As depicted in Reaction Scheme 2, below, γ-valerolactone (GVL) can be obtained from hydrogenation of levulinic acid, another platform molecule derived from monosaccharide dehydration. In addition, GVL is an important platform molecule used for the production of chemicals and fuels.[21, 22] Other γ-lactones with higher molecular weights can be obtained from GVL, as described elsewhere,[23, 24] or by ring closing of unsaturated acid.[25] Thus, in addition to using GVL, the examples below also disclose reactions using γ-hexalactone (GHL), γ-octalactone (GOL) and γ-undecalactone (GUL). Similar to GVL, THF can be derived from biomass from the decarbonylation and hydrogenation of furfural, a product of xylose dehydration.[26, 27]

closed herein are methodologies to upgrade the HMF to FDCA, in an integrated process that can start from starch, cellulose, glucose or fructose yielding HMF, FDCA, or other value-added chemicals as the final products.

Reaction Scheme 2

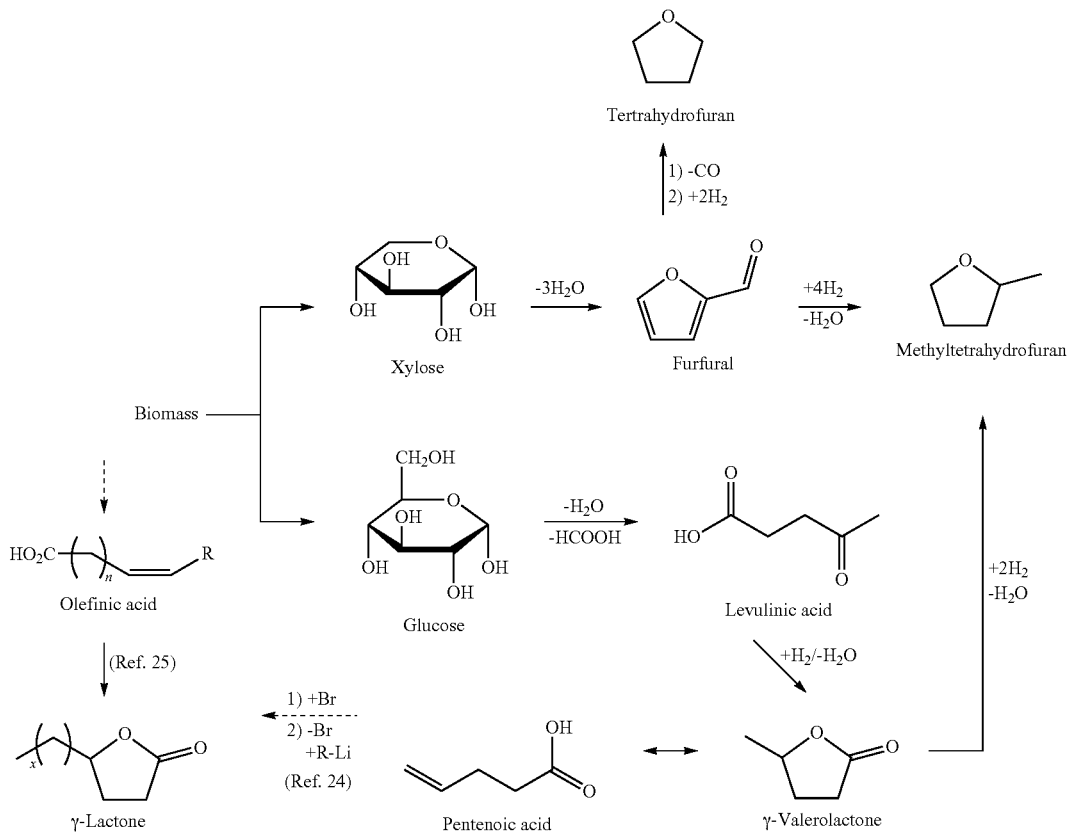

Thus, in the present method, lactones, hydrofurans and hydropyrans are used to produce HMF and furfural from biomass-derived starch, cellulose, glucose and/or fructose using homogeneous or heterogeneous catalysts. Also dis- FIG. 6 is a schematic diagram of a second version of the process in which a monophasic reaction using homogeneous catalysts is used to produce HMF from C6 sugars derived from biomass.

Figure 6:
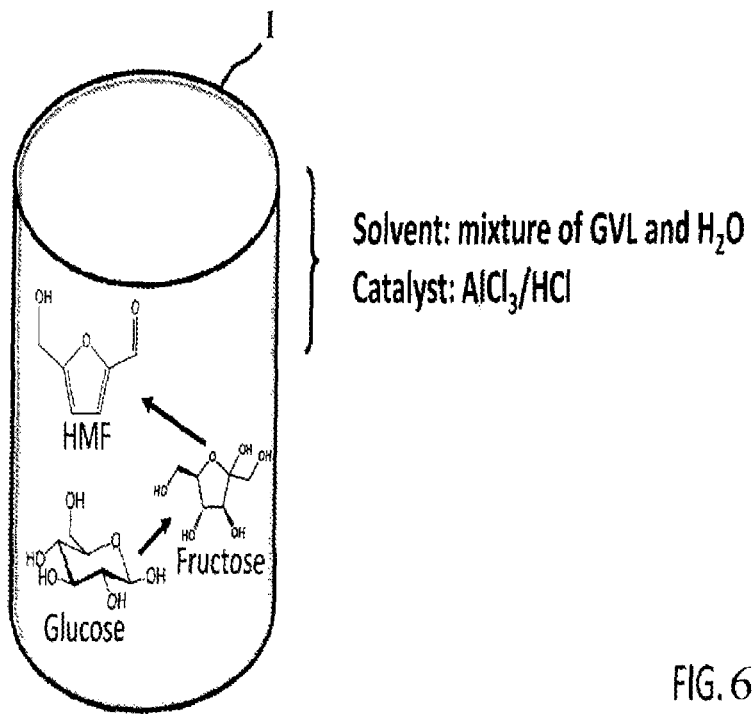
Figure 7:
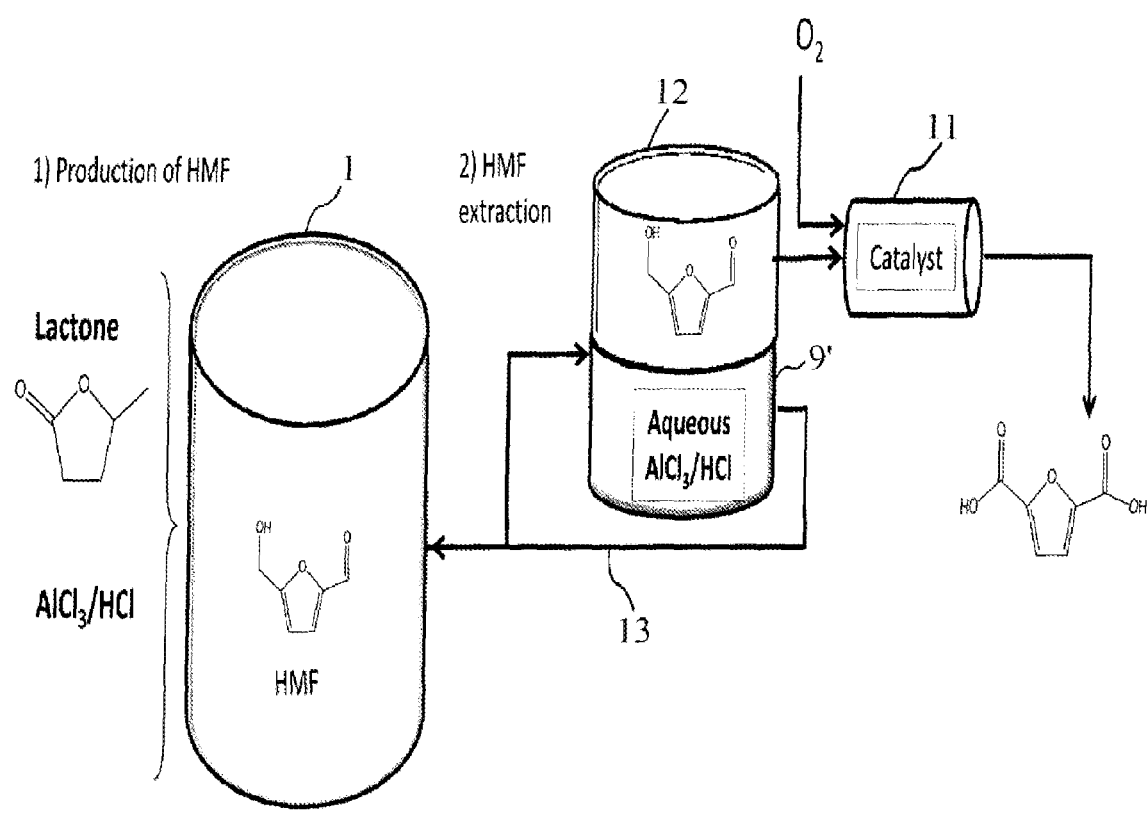

FIG. 7 is a schematic diagram as depicted in FIG. 6, and further depicting downstream oxygenation of the HMF to yield FDCA.

Figure 8:
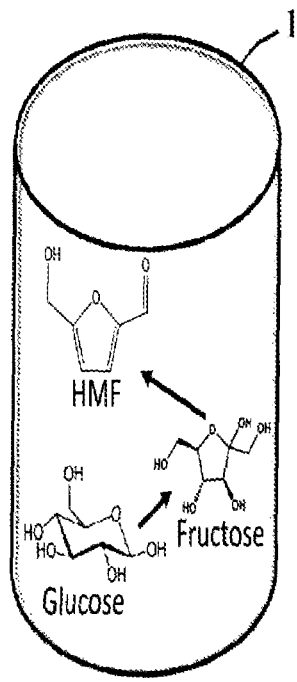

FIG. 8 is a schematic diagram of a third version of the process in which a monophasic reaction using heterogeneous catalysts is used to produce HMF from C6 sugars derived from biomass.

Figure 9:
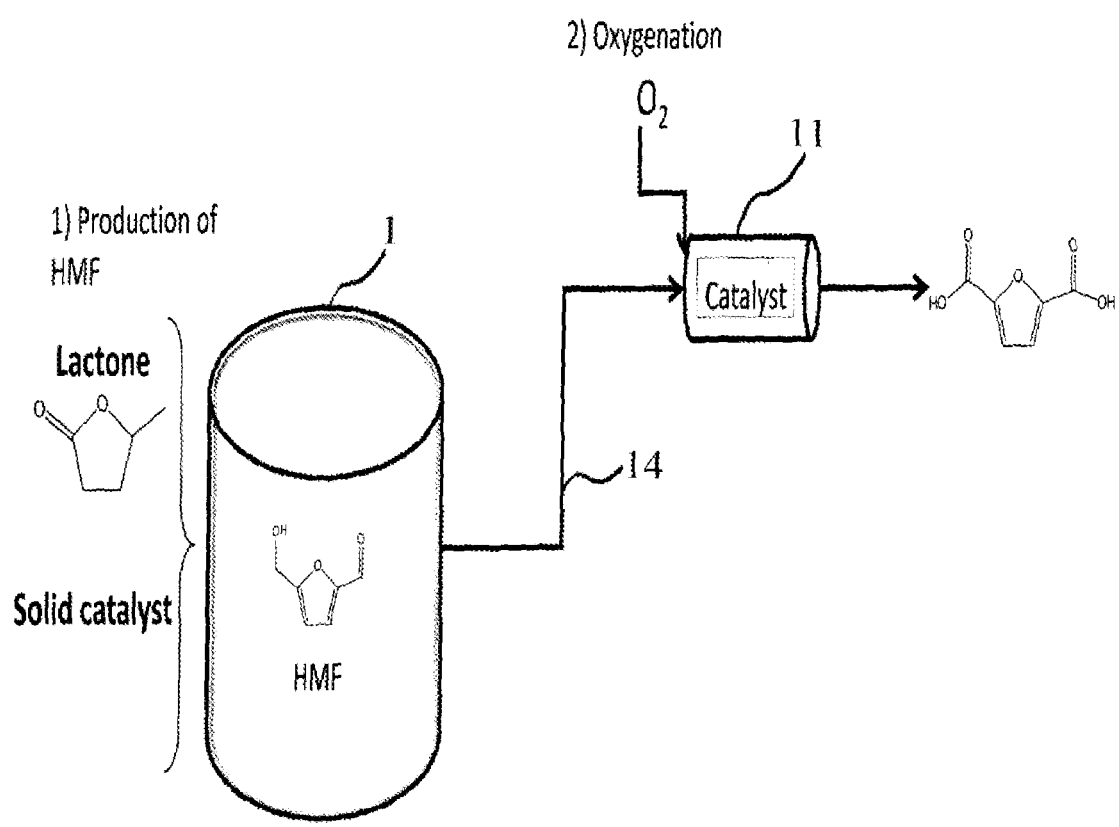

FIG. 9 is a schematic diagram as depicted in FIG. 8, and further depicting downstream oxygenation of the HMF to yield FDCA.

Figure 10:
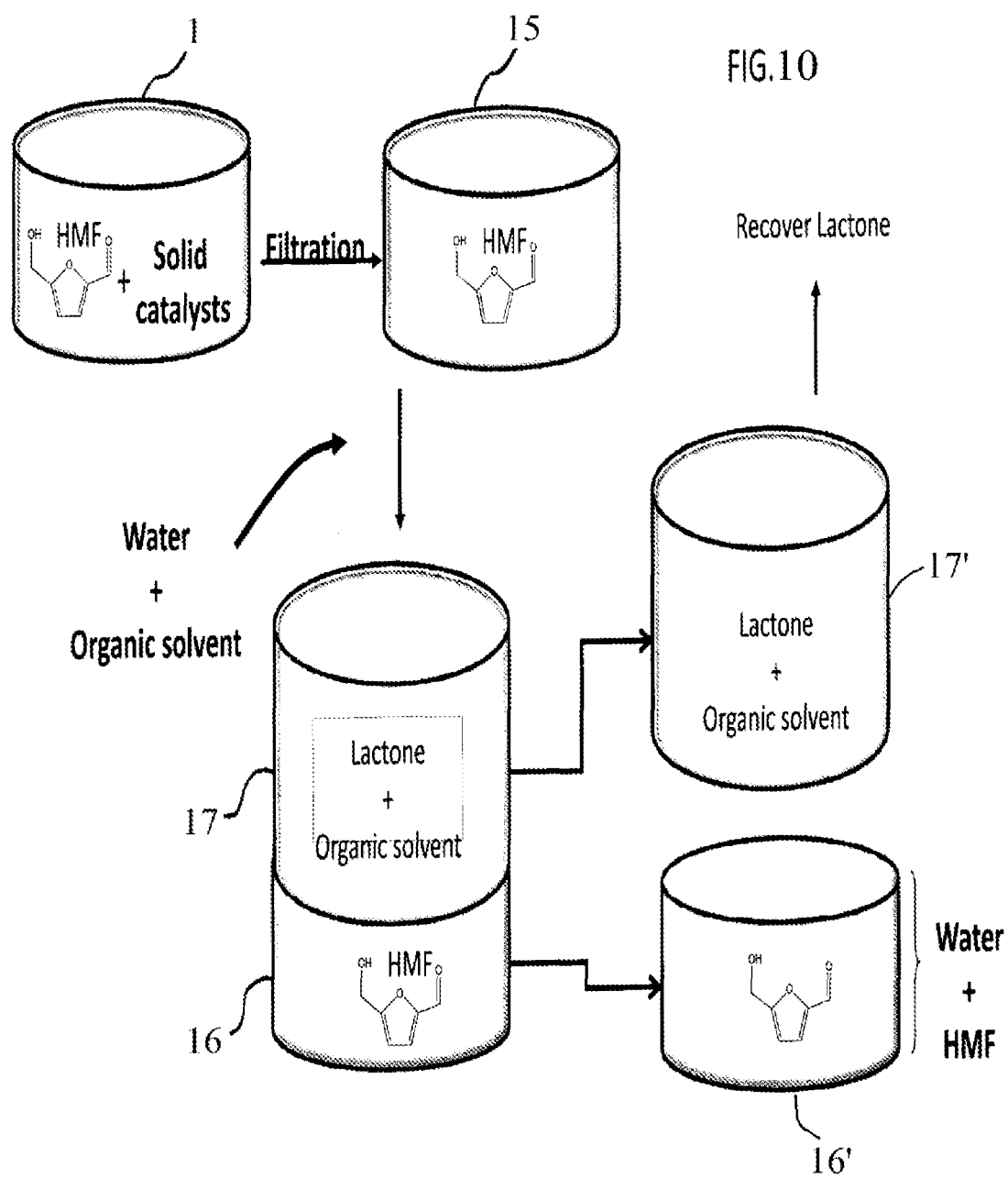

FIG. 10 is a schematic diagram as depicted in FIG. 8, and further depicting downstream extraction of the HMF into an aqueous solution.

Figure 11:
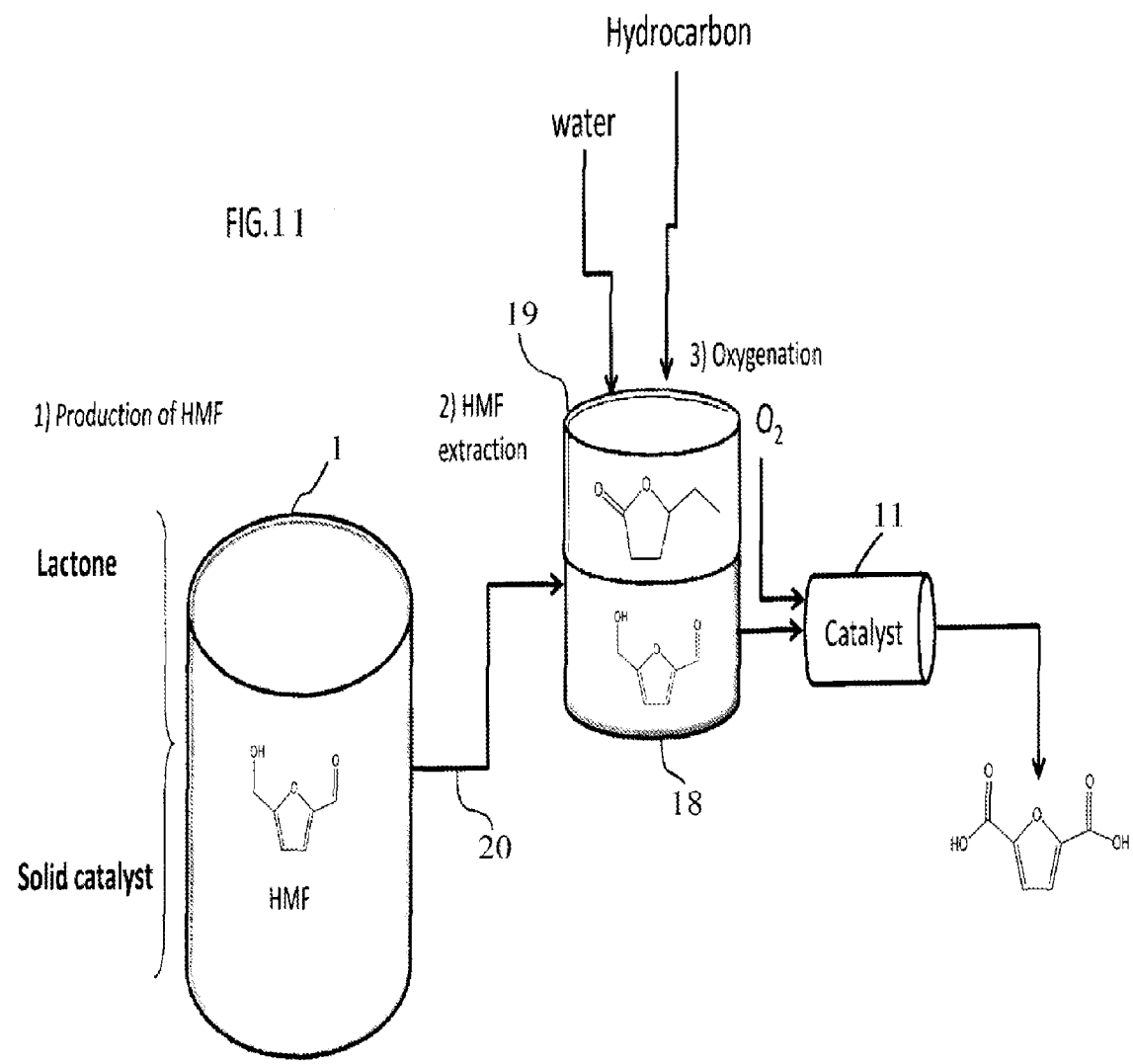

FIG. 11 is a schematic diagram of depicting oxidation of HMF present in the aqueous phase of a biphasic system to yield FDCA.

Figure 12:
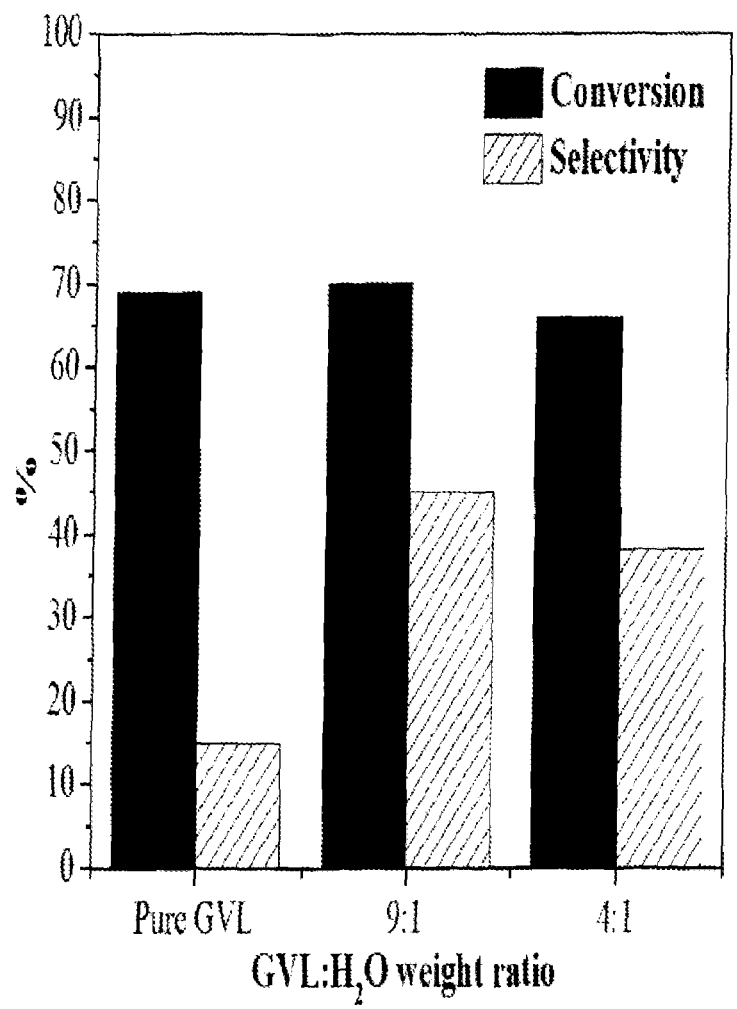

FIG. 12 is a histogram depicting the effect of water content on glucose conversion to HMF using the present process.

Figure 13A:
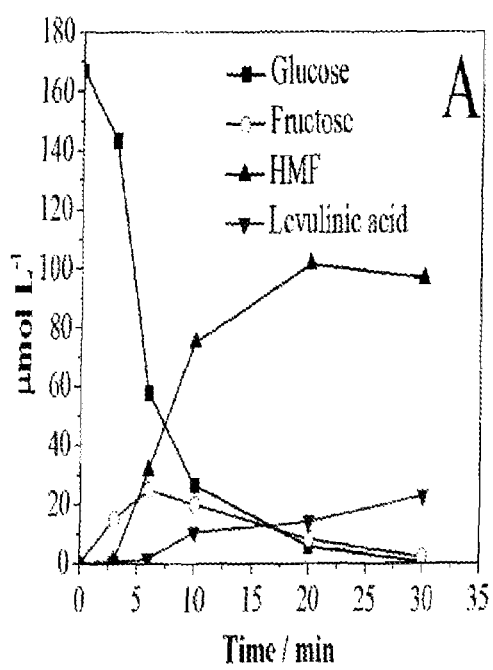
Figure 13B:
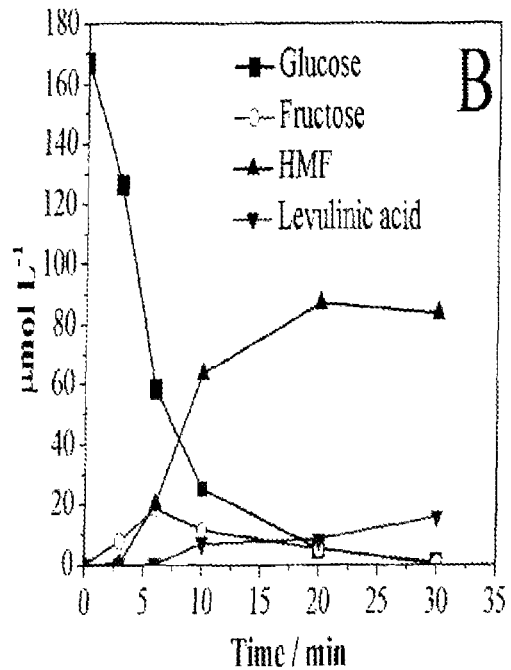
Figure 13C:
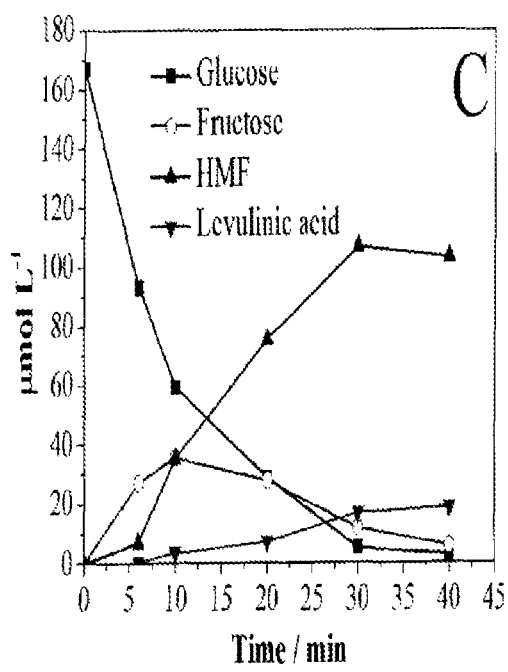
Figure 13D:
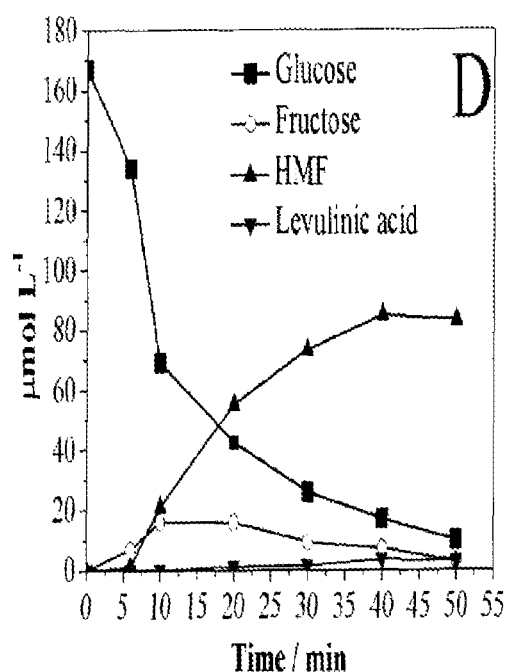
Figure 13E:
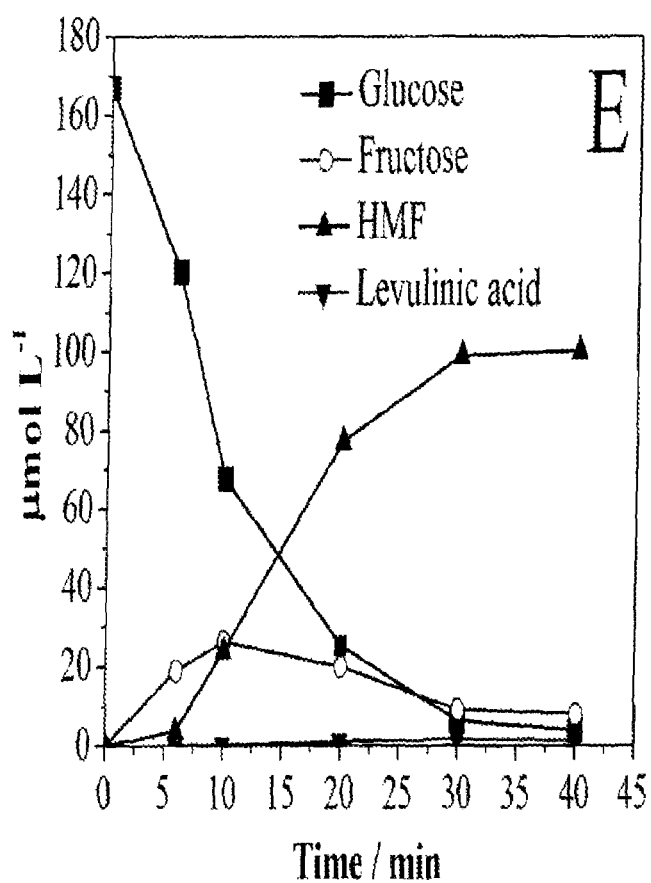

FIGS. 13A, 13B, 13C, 13D, and 13E depict glucose dehydration in various solvents using the disclosed process. FIG. 13A depicts glucose dehydration in GVL. FIG. 13B depicts glucose dehydration in GHL. FIG. 13C depicts glucose dehydration in THF. FIG. 13D depicts glucose dehydration in MTHF. FIG. 13E depicts glucose dehydration in THF:MTHF (1:1). All solvents contained 10% water. For all reactions: 2 wt % glucose; 0.05 g Sn-β; 0.05 g Amb-70; T=130° C.

Figure 14:
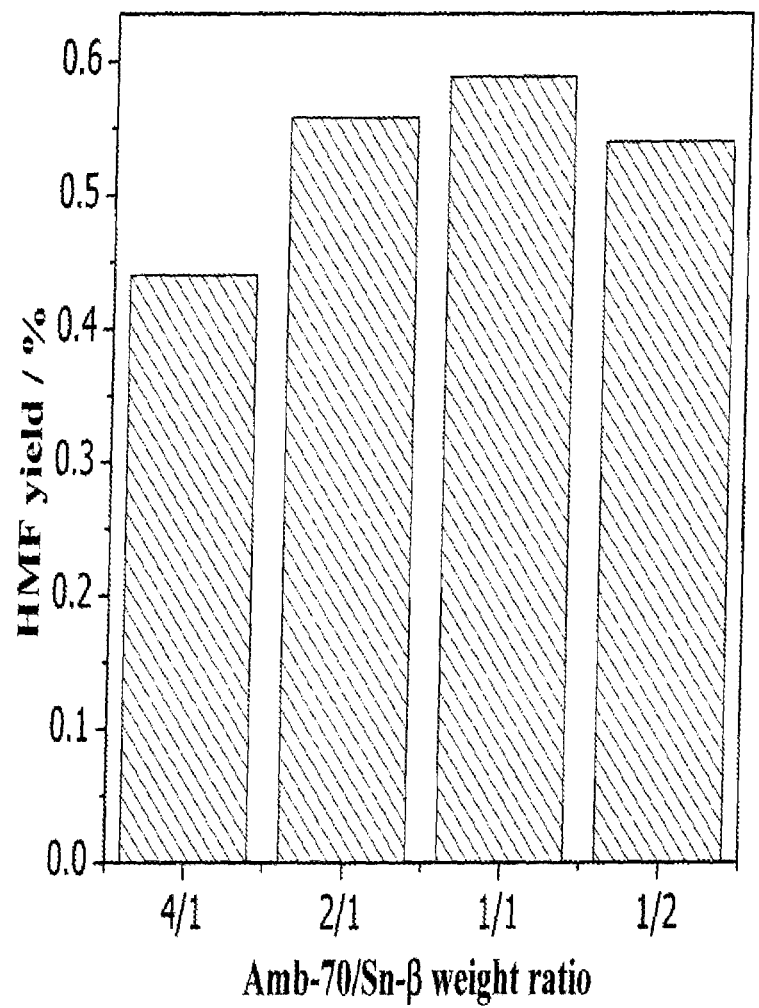

FIG. 14 is a histogram depicting the effect of Amb-70/Sn-β weight ratio on the HMF yield using glucose and GVL:$H_2O$ (9:1) as the solvent.

DETAILED DESCRIPTION

Abbreviations and Definitions

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

"Biomass-derived"=Compounds or compositions fabricated or purified from biomass. Glucose and HMF for use in the disclosed method may be biomass-derived.

Brønsted-Lowry Acid/Base=A Brønsted-Lowry acid is defined herein as any chemical species (atom, ion, molecule, compound, complex, etc.), without limitation, that can donate or transfer one or more protons to another chemical species. Mono-protic, diprotic, and triprotic acids are explicitly included within the definition. A Brønsted-Lowry base is defined herein as any chemical species that can accept a proton from another chemical species. Included among Brønsted-Lowry acids are mineral acids, organic acids, heteropolyacids, solid acid catalysts, zeolites, etc. as defined herein. Note that this list is exemplary, not exclusive. The shortened term "Brønsted" is also used synonymously with "Brønsted-Lowry."

"Carbohydrate" is defined herein as a compound that consists only of carbon, hydrogen, and oxygen atoms, in any ratio.

"$C_5$ carbohydrate" refers to any carbohydrate, without limitation, that has five (5) carbon atoms. The definition includes pentose sugars of any description and stereoisomerism (e.g., D/L aldopentoses and D/L ketopentoses). $C_5$ carbohydrates include (by way of example and not limitation) arabinose, lyxose, ribose, ribulose, xylose, and xylulose.

"$C_6$ carbohydrate" refers to any carbohydrate, without limitation, that has six (6) carbon atoms. The definition includes hexose sugars of any description and stereoisomerism (e.g., D/L aldohexoses and D/L ketohexoses). C6 carbohydrates include (by way of example and not limitation) allose, altrose, fructose, galactose, glucose, gulose, idose, mannose, psicose, sorbose, tagatose, and talose.

"Cellulose" refers to a polysaccharide of glucose monomers (($C_6H_{10}O_5)_n$); "cellulosic biomass" refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose, as does hemicellulose.

"Dehydration catalyst" means any catalyst, without limitation, whether now known or developed in the future, capable of removing water from organic compounds.

"Glucose-containing oligomers, glucose-containing polymers, Glucose-containing reactant, C6-containing reactant"=Any chemical species, having any type of intramolecular bond type, that comprises a glucose unit. The definition explicitly includes glucose-containing disaccharides (such as, but not limited to, sucrose, lactose, maltose, trehalose, cellobiose, kojibiose, nigerose, isomaltose, β,β-trehalose, α,β-trehalose, sophorose, laminaribiose, gentiobiose, turanose, maltulose, palatinose, gentiobiulose, etc.), trisaccharides (such as, but not limited to, isomaltotriose, nigerotriose, maltotriose, maltotriulose, raffinose, etc.), and larger oligosaccharides and polysaccharides, as well as large and more complex glucose-containing polymers and carbohydrates, such as, but not limited to, starch, amylase, amylopectin, glycogen, cellulose, hemicelluloses (e.g., xyloglucan, glucomannan, etc.), lignocellulose, and the like. Linear, branched, and macrocyclic oligomers and polymers containing glucose are explicitly included within the definition.

"Heteropolyacid"=A class of solid-phase acids exemplified by such species as $H_4SiW_{12}O_{40}$, $H_3PW_{12}O_{40}$, $H_6P_2W_{18}O_{62}$, $H_{3+x}PMo_{12-x}V_xO_{40}$ and the like. Heteropolyacids are solid-phase acids having a well-defined local structure, the most common of which is the tungsten-based Keggin structure. The Keggin unit comprises a central $PO_4$ tetrahedron, surrounded by 12 $WO_6$ octahedra. The standard unit has a net (⁻3) charge, and thus requires three cations to satisfy electroneutrality. If the cations are protons, the material functions as a Brønsted acid. The acidity of these compounds (as well as other physical characteristics) can be "tuned" by substituting different metals in place of tungsten in the Keggin structure. See, for example, Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical Chemistry B*, 102:10817-10825.

"Homogeneous catalyst"=A catalyst that exists in the same phase (solid, liquid, or gas) as the reactants under reaction conditions. "Heterogeneous catalyst"=A catalyst that exists in a different phase than the reactants under reaction conditions.

"Hydrofuran" is used herein to refer to any unsubstituted or substituted cyclic ester having a single oxygen heteroatom in the ring, and having five total atoms in the ring and which is derived from furanic compounds. Hydrofurans that are miscible in water, such as tetrahydrofuran (THF), are more appropriate for use in the monophasic reactions described herein. In the biphasic reactions, any hydrofuran may be used.

"Hydropyran" is used herein to refer to any unsubstituted or substituted cyclic ester having a single oxygen heteroatom in the ring, and having six total atoms in the ring and which is derived from pyranic compounds. Hydropyrans miscible in water are more appropriate for use in the monophasic reactions described herein. In the biphasic reactions, any hydropyran may be used.

"Lactone" as used herein refers to an unsubstituted or substituted cyclic ester, having a single oxygen heteroatom in the ring, and having from four to six total atoms in the ring—i.e., beta, gamma, and delta lactones, derived from any corresponding C4 to C16 carboxylic acid. Thus, as used herein, the term "lactone" explicitly includes (without limitation) unsubstituted and substituted beta and gamma-butyrolactone and beta-, gamma-, and delta-valerolactones to beta-, gamma, and delta-hexadecalactones. Some lactones are miscible in water, such as GVL; other lactones have more limited solubility in water. Those lactones that can dissolve at least about 1 wt % water, and more preferably at least about 5 wt % (or more) of water (up to miscible) are suitable for use in the monophasic reactions described herein. In the other hand, any lactone is suitable to biphasic system.

As used herein, the term "oxygenation catalyst" refers without limitation to any catalyst, now known or developed in the future, homogenous or heterogeneous, that catalyzes the oxygenation of alcohols and/or aldehydes. The oxidation reaction may be partial or complete (i.e., oxidation from alcohol to aldehyde or ketone; or oxidation from alcohol to carboxylic acid). Oxidation catalysts may comprise, but are not limited to, alkaline earth metals, rare earth metals, chromium, manganese, molybdenum, tungsten, tin, rhenium, bismuth, indium, phosphorus, iron, cobalt, nickel, ruthenium, rhodium, palladium, osmium, iridium, platinum, noble metals generally, oxides thereof, derivatives thereof, mixtures thereof, or combinations thereof.

The oxygenation catalysts may be disposed on a catalyst support material, such as a refractory oxide. For example, the refractory oxide can be alumina, particularly alpha alumina, zirconia, titania, hafnia, silica; or mixtures thereof. The catalyst support material can be or can include rare earth-modified refractory metal oxides, where the rare earth may be any rare earth metal, for example, lanthanum or yttrium; and/or alkali earth metal-modified refractory oxides. The catalyst support material can be categorized as materials having a substantially stable surface area at reaction conditions, for example, a surface area that is not substantially altered by reaction conditions or altered in a way that affects the reaction.

FA=formic acid. FDCA=2,5-furandicarboxylic acid. GHL=gamma-hexalactone. GOL=gamma-octalactone. GUL=gamma-undecalactone. GVL=gamma-valerolactone (γ-valerolactone). HMF=5-hydroxymethylfurfural. LA=levulinic acid. SA=sulfuric acid. Mineral acid=any mineral-containing acid, including (by way of example and not limitation), hydrochloric acid, nitric acid, phosphoric acid, SA, boric acid, hydrofluoric acid, hydrobromic acid, and the like. Organic acid=any organic acid, without limitation, such as toluenesulfonic acid, formic acid, acetic acid, trifluoroacetic acid, oxalic acid, and the like. PET=polyethylene terephthalate. CP=cyclopentane. MCP=methylcyclopentane. THF=Tetrahydrofuran. MTHF=2-methyltetrahyddrofuran.

Second organic solvent=an aprotic, generally low-polarity organic solvent, including, but not limited to saturated hydrocarbons (linear, branched, cyclic alkanes such as pentane, hexane, heptane, octane, cyclohexane, and the like), perhalo-alkanes (e.g., carbon tetrachloride, hexachloroethane, hexafluoroethane, etc.), aromatic hydrocarbons, such as benzene and alkylbenzenes of any description (e.g., mono-, di-, tri-, tetra-, penta-, and hexa-$(C_{1-6}$-alkyl)-benzenes, such as toluene, xylene, cumene, cymene, ethylbenzene, and the like). Also specifically included within the definition are linear, branched or cyclic alkanes; linear, branched or cyclic alkenes; linear, branched or cyclic ketones; linear, branched or cyclic alcohols; aromatic hydrocarbons; and substituted or unsubstituted phenols.

Lewis Acid/Base=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

The Lewis acid (also referred to as the Lewis acid catalyst) may be any Lewis acid based on transition metals, lathanoid metals, and metals from Group 4, 5, 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, (alkyl)$AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula $MX_4$; wherein M is Group 4, 5, or 14 metal, and X is a halogen independently selected from the group consisting of fluorine, chlorine, bromine, and iodine, preferably chlorine. X may also be a psuedohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a psuedohalogen. Non-limiting examples include benzyltitanium trichloride, dibenzyltitanium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_n R'_m X_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a psuedohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX_3$; wherein M is a Group 13 metal and X is a halogen independently selected from the group consisting of fluorine, chlorine, bromine, and iodine, preferably chlorine. X may also be a psuedohalogen. Non-limiting examples include aluminum trichloride, boron trifluoride, gallium trichloride, indium trifluoride, and the like.

The Group 13 Lewis acids useful in method may also have the general formula: $MR_n X_{3-n}$ wherein M is a Group 13 metal; R is a monovalent hydrocarbon radical selected from the group consisting of $C_1$ to $C_{12}$ alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a psuedohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_n R'_m X_{3-(m+n)}$; wherein M is a Group 13 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3; m is an number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_n R'_m X_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lathanoid metal halides, and Group 5, 13, and 14 metal halides. Preferred among the metal halides are metal chlorides. Preferred transition metal chlorides include, but are not limited to, $TiCl_4$, $VCl_3$. and the like. Preferred Group 13 and 14 metal halides and chlorides include, but are not limited to, $BF_3$, $AlCl_3$, $SnCl_4$, $InCl_3$, and $GaCl_3$. Preferred lanthanoid chlorides include, but are not limited to, $LaCl_3$, $DyCl_3$ and $YbCl_3$.

"Noble metal" is used herein to include ruthenium, rhodium, palladium, silver, osmium, iridium, platinum, gold, mercury, rhenium, and copper. Other corrosion-resistant metals that can be used as catalysts in the subject process include titanium, niobium, and tantalum.

The terms "solid acid" and "solid acid catalyst" are used synonymously herein and can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropolyacids, acid resin-type catalysts, mesoporous silicas, acid clays, sulfated zirconia, molecular sieve materials, zeolites, and acidic material on a thermostable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4^{2-}$ or $SO_3H$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. (These types of resins are designated herein as "Amb" resins, followed by a numeric identifier of the specific sub-type of resin where appropriate.) The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Solid catalysts can be in any shape or form now known or developed in the future, such as, but not limited to, granules, powder, beads, pills, pellets, flakes, cylinders, spheres, or other shapes.

Supports for metal catalysts can be any suitable support (now known or developed in the future) that is sufficiently robust to withstand the reaction conditions disclosed herein. Suitable catalyst supports include, by way of example and not limitation, alumina, carbon, ceria, magnesia, niobia, silica, titania, zirconia, zeolites (preferably, Y, ZSM 5, MWW and beta), hydrotalcite, molecular sieves, clays, iron oxide, silicon carbide, aluminosilicates, and modifications, mixtures or combinations thereof.

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

Figure 1:
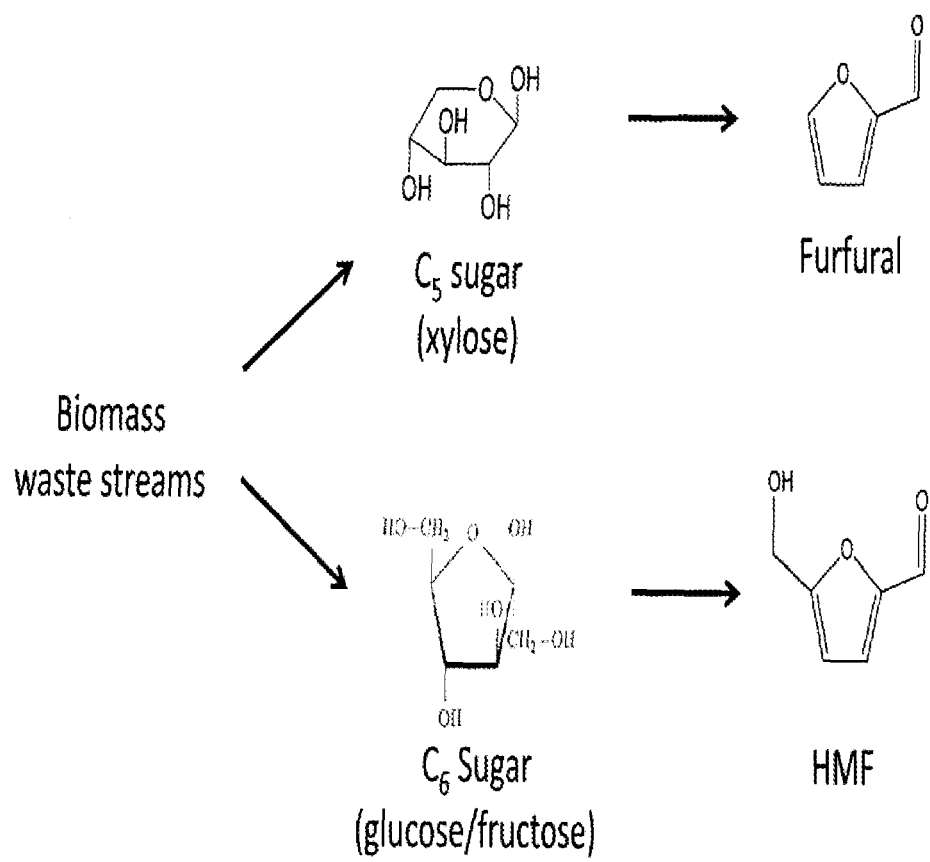
FIG. 1 is a reaction scheme depicting conversion of C5 sugars from biomass into furfural and conversion of C6 sugars from biomass into hydroxymethylfurfural (HMF).
Figure 2:
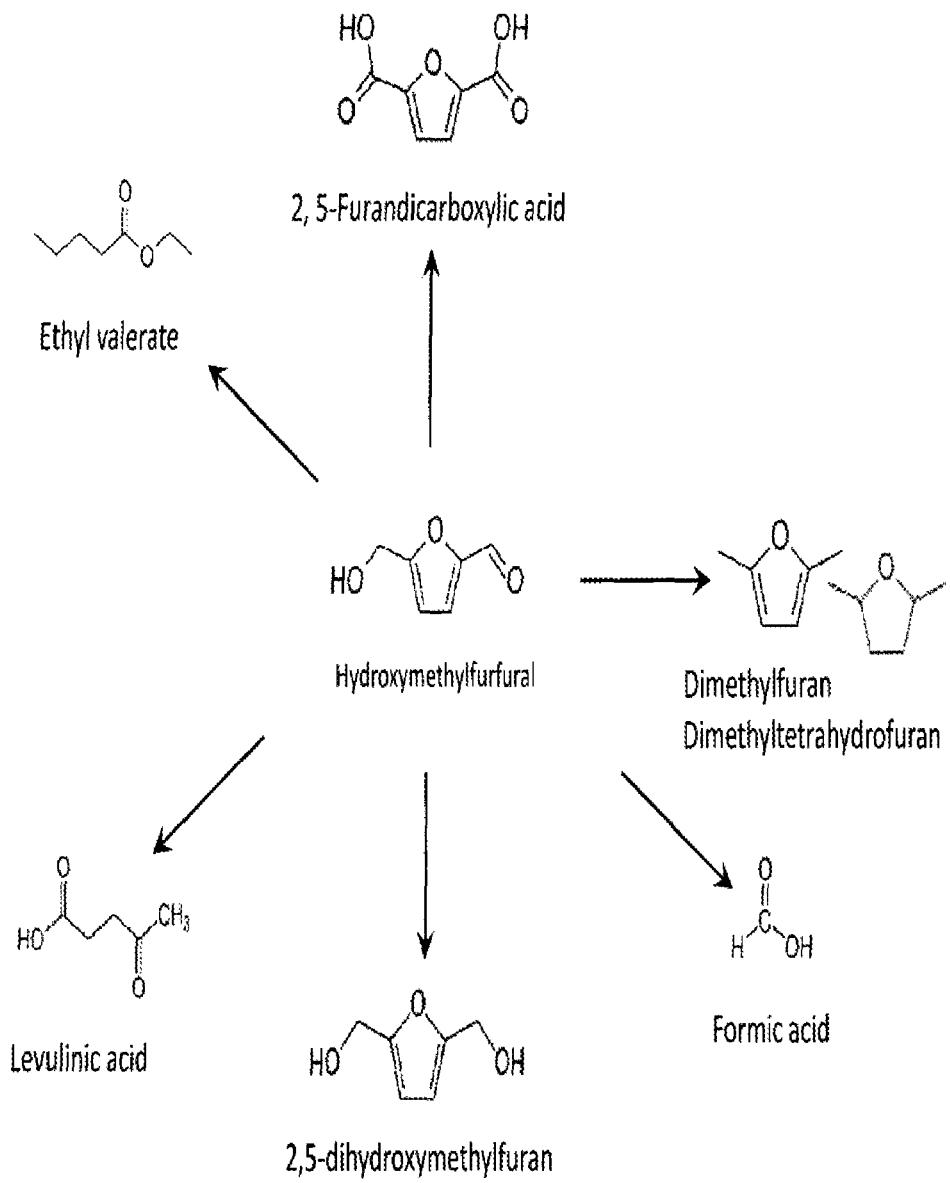
FIG. 2 is a reaction scheme depicting various downstream, value-added chemicals that can be made from furfural and/or HMF.
Figure 3:
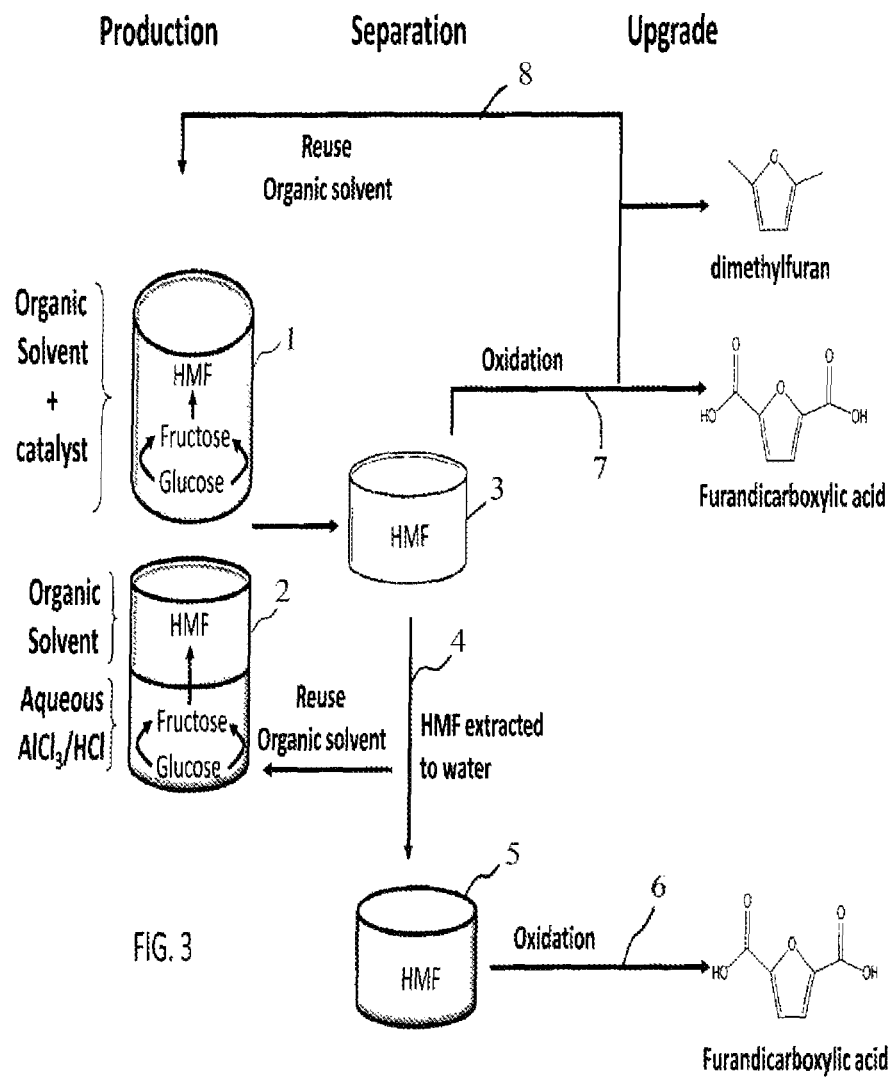
FIG. 3 is a schematic overview of the process of using organic solvent derived from biomass to convert C6 sugars from biomass (typically glucose and fructose) into HMF and other downstream, value-added chemicals.

Overview and Schematic Depiction of Reaction Types:

FIG. 3 depicts a schematic overview of the process to produce HMF, as well as to upgrade the HMF to value-added, downstream chemicals such as dimethylfuran (DMF) and furandicarboxylic acid (FDCA). As shown in FIG. 3, the production of HMF can take place in either a monophasic reaction solution 1 or in a biphasic reaction solution 2 having an aqueous reaction phase and an organic extraction phase. Both approaches will be discussed in greater detail below. In both approaches, and acid catalyst is used and the organic solvent itself is derived from biomass. It is preferred that the organic solvent in either 1 or 2 be a lactone, a hydrofuran or a hydropyran as defined herein, and most preferably a gamma-lactone that can be, but not only, derived from a corresponding C5 to C16 carboxylic acid (i.e., gamma valerolactone to gamma hexadecalactone) and tetrahydrofuran that can be obtained, but not only, from furfural.

In reactors 1 and 2, biomass-derived C6 sugars are converted to HMF. The HMF formed in reactor 1 or 2 may be concentrated, separated or otherwise purified at 3. If the HMF remains admixed with organic solvent, the HMF may be extracted 4 into water to yield an aqueous solution of HMF 5. From here, the aqueous solution of HMF 5 may be oxidized 6 to yield FDCA. The organic solvent that spontaneously phase separates from the aqueous solution of HMF may be recycled into reactor 2. Alternatively, the HMF at 3 may be directly oxygenated 7, with or without any intervening steps, to yield downstream products such as FDCA. The organic solvent may be captured and recycled into reactor 1 or 2 as shown at 8.

Figure 4:
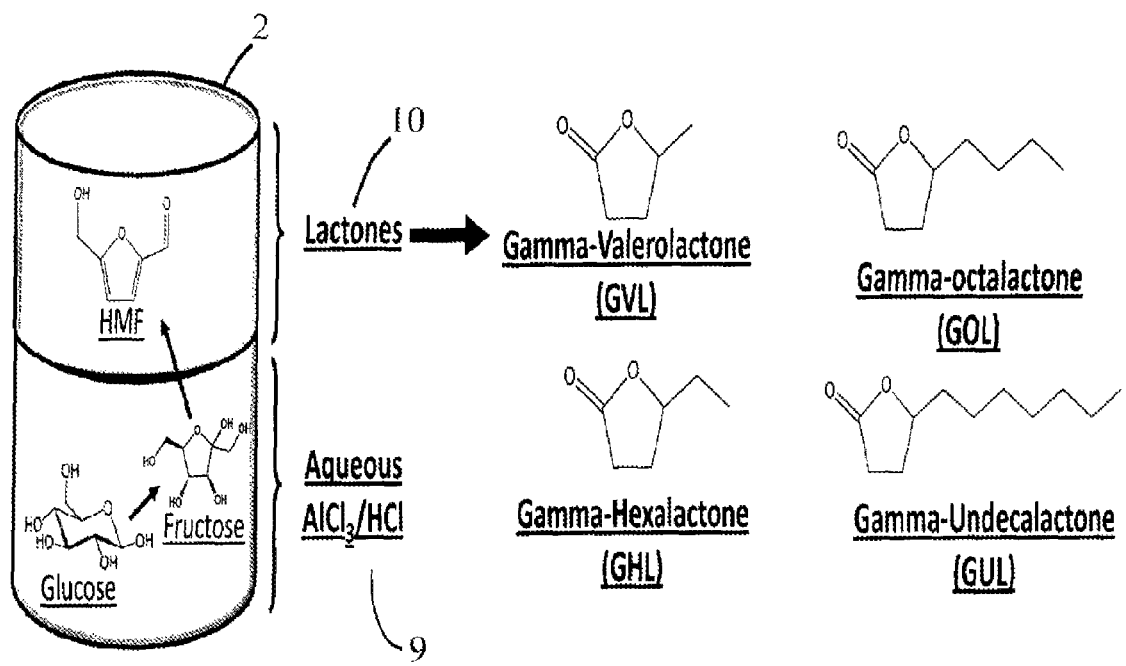
FIG. 4 is a schematic diagram of a first version of the process in which a biphasic reaction is used to produce HMF from C6 sugars derived from biomass. The upper, organic layers comprises one or more lactones, such as (and without limitation) gamma-valerolactone (GVL), gamma-octlactone (GOL), gamma-heaxlactone (GHL), and gamma-undecalactone (GUL).

FIG. 4 is an isolated view of reactor 2 as shown in FIG. 3. Here, the reaction to yield HMF takes place in a biphasic system comprising a lower aqueous phase 9 and an upper organic phase 10 that comprises a lactone, preferably a biomass-derived lactone, more preferably a biomass-derived gamma-lactone, and most preferably biomass-derived GVL, GHL, GOL, and/or GUL. As shown in FIG. 4, biomass-derived glucose isomerizes to fructose and is then converted to HMF in the presence of an acid catalyst in the aqueous phase 9. The HMF so formed then is extracted into lactones in the organic phase 10.

Figure 5:
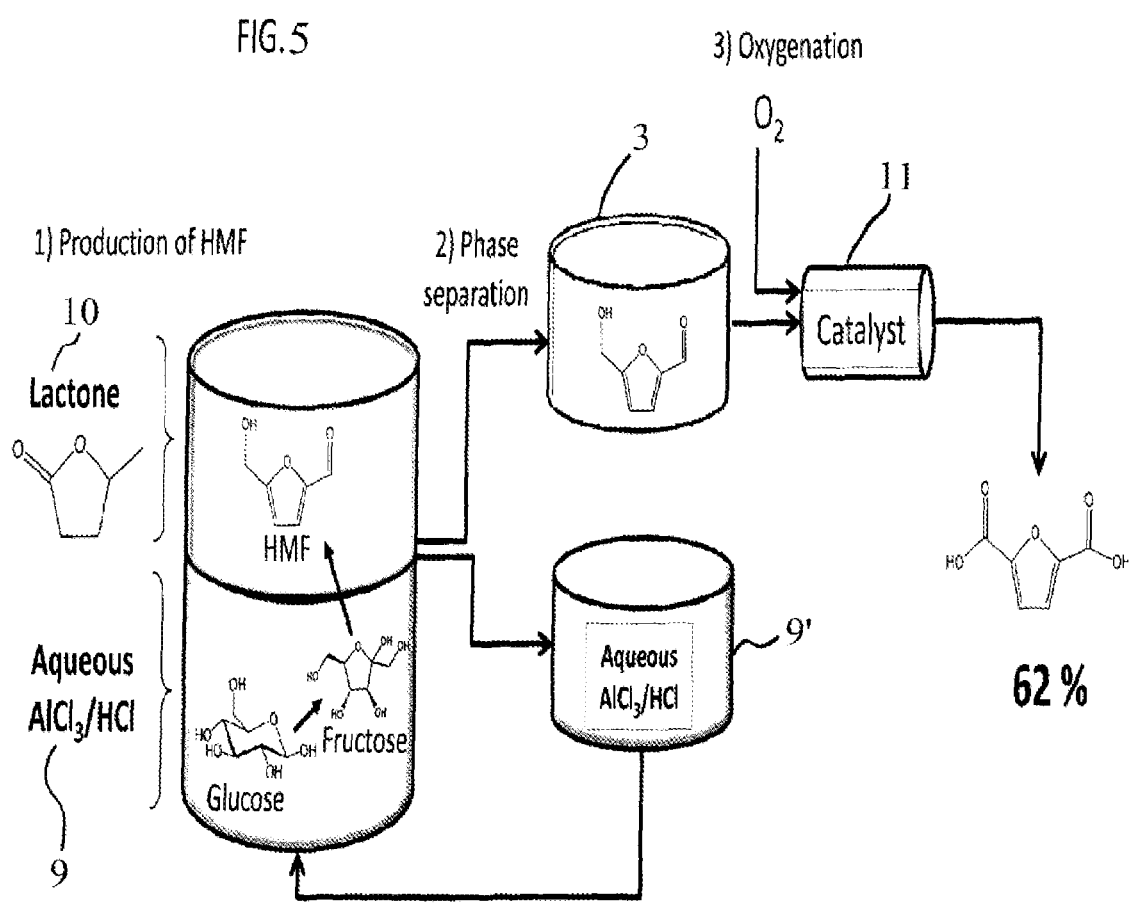
FIG. 5 is a schematic diagram as depicted in FIG. 4, and further depicting downstream oxygenation of the HMF to yield 2,5-furandicarboxylic acid (FDCA).

FIG. 5 is an isolated view of the process using a biphasic reactor 2 and a hydrogenation catalyst 11 to convert C6 sugars to HMF and to convert the HMF to FDCA. Yields of 62% and better are typical. Thus, the reaction to yield HMF takes place in a biphasic system comprising a lower aqueous phase 9 and an upper organic phase 10 that comprises a lactone. C6 sugars in the aqueous phase are converted to HMF which is then extracted into the lactone-containing organic phase 10. The two phases are then separated to yield an organic phase 3 containing the HMF and an aqueous phase 9' containing water and the acid catalyst. The HMF at 2 is then subjected to the oxygenation reaction 30.

FIG. 6 is an isolated view of reactor 2 as shown in FIG. 3. Here, the reaction to yield HMF takes place in a monophasic system comprising a lactone, a hydrofuran or a hydropyran that is miscible with water or has at least 5% solubility in water. FIG. 6 exemplifies the use of the gamma-lactone GVL, which is miscible with water and can be obtained from biomass. For illustration purposes only, the acid catalyst is depicted as $AlCl_3$ and HCl. As noted in the figure a number of advantages are realized by using a monophasic system. Homogeneous and/or heterogeneous catalysts may be used. There are no mixing concerns because the reaction solution is monophasic. HMF is obtained in very high yields. The GVL solvent (was well as other suitable lactones, hydrofurans, hydropyrans) have very low toxicity.

A schematic diagram depicting using the monophasic reaction system to make FDCA from biomass-derived sugars is shown in FIG. 7. Thus, reactor 1 is used to produce HMF from glucose/fructose in a monphasic system. The exemplary lactone depicted as GVL, and an exemplary $AlCl_3$/HCl acid catalyst is also shown. The HMF is then extracted into an organic phase 12 and an acidic, aqueous phase 9'. The HMF present in phase 12 is then oxidized using catalyst 11. The aqueous, acidic phase 9' may optionally be recycled 13 back into reactor 1.

FIG. 8 is identical to FIG. 6, with the exception that a solid acid catalyst (i.e., a heterogeneous catalyst) is used. Again, the reaction solvent comprises a monophasic solution of a lactone and water. One or more solid acid catalysts are used to drive the formation of HMF from sugars in the reactant solution. Exemplary solid acid catalysts are noted in the figure. On top of the advantages listed in FIG. 6, using solid acid catalysts as depicted in FIG. 8, in conjunction with a monophasic reaction, means there is no need of phase separations and the solid acid catalysts are easily removed by simple filtration.

This enables very efficient reactions to yield HMF and downstream products, such as the reactions shown in FIGS. 9, 10 and 11. In FIG. 9, the HMF is formed in the monophasic solution using a solid acid catalyst as described herein. The catalyst is then easily removed and the HMF solution transferred via conduit 14 to contact an oxygenation catalyst 11 to yield FDCA.

Alternatively, as shown in FIG. 10, a similar approach using solid acid catalysts may be used to yield an aqueous solution of HMF as the final products. Here, the HMF is formed from biomass-derived sugars in a lactone-containing, monophasic solvent using a solid acid catalyst 1. The solid catalyst is then removed by filtration to yield the HMF in a lactone-containing solvent 15. A mixture of water and an organic solvent is then added to 15 to cause a spontaneous phase separation in which the HMF is extracted into the aqueous phase 16. The two phases are then separated to yield an aqueous solution of HMF 16' and an organic solution containing the lactone 17'. The lactone may optionally be recovered and recycled back into reactor 1.

FIG. 11 depicts the same approach as described for FIG. 10, with the added downstream step of converting the HMF in the aqueous phase 18 to FDCA using an oxygenation catalyst 11. Thus, in FIG. 11, the HMF is formed from biomass-derived sugars in a lactone-containing, monophasic solvent using a solid acid catalyst 1. The solid catalyst is the removed by filtration (20) and water and an organic solvent (shown as "hydrocarbon" in FIG. 11) are then added to cause a spontaneous phase separation in which the HMF is extracted into an aqueous phase 18 and a lactone-containing organic phase 19. The HMF is then oxidized at 11 to yield FDCA.

In the present process, the HMF is directly oxidized to FDCA without isolating, concentrating or purifying the HMF in any fashion. The HMF is oxidized to FDCA by contacting the HMF in the reaction solution with molecular oxygen over a supported metal catalyst. At least a portion of the FDCA is then extracted from the reaction mixture by adding to the reaction an amount of an aprotic, low-polarity organic solvent, such as toluene. A sufficient amount of the organic solvent is added so that the reaction solution spontaneously partitions into a two-phase system: a first phase rich in GVL and the added organic solvent; and a second phase rich in FDCA.

EXAMPLES

The following examples are included solely to provide a more complete description of the process described and claimed herein. The examples do not limit the scope of the process in any fashion.

Solvents and Catalysts Used:

Table 1 depicts the various organic solvents that were used in the examples. Note that the list of solvents is exemplary and not limiting.

TABLE 1

Solvents used in the examples.

| Solvent name | Abbreviation | Structure |
| --- | --- | --- |
| Gamma-valerolactone | GVL | 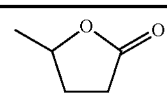 |
| Gamma-hexalactone | GHL | 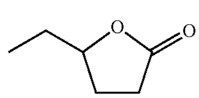 |

TABLE 1-continued

Solvents used in the examples.

| Solvent name | Abbreviation | Structure |
| --- | --- | --- |
| Gamma-octalactone | GOL | 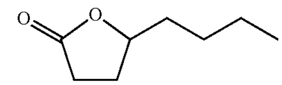 |
| Gamma-undecalactone | GUL | 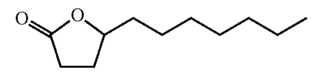 |
| Tetrahydrofuran | THF | 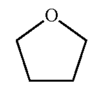 |
| sec-Butylphenol | SBP | 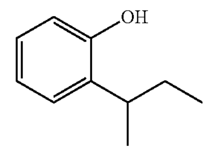 |

Brønsted Solid Acid Catalysts:

"AMBERLYST"-70®-brand solid acid catalyst were obtained from The Dow Chemical Company (Midland, Mich., USA). "AMBERLYST"-brand resins are a family of commercial catalysts comprising a backbone of cross-linked polystyrene modified with sulfonic acid groups. "AMBERLYST" is a registered trademark of Rohm and Haas Company, Philadelphia, Pa. (a wholly owned subsidiary of The Dow Chemical Company).

Lewis Acid Catalysts:

Sn-SBA-15: Synthesized as described by Shah et al. [39]. SBA-15 is a mesoporous structure of amorphous silica. Tin cations were inserted in tetrahedral positions into the silica framework in a ratio Si/Sn=40.

$SnO_2/Al-\beta$: Al-β Zeolite is a crystalline microporous aluminosilicate mineral that possesses well defined structure type with distinct pore dimensions and pore connectivity. The presence of aluminum in tetrahedral positions generated negative structural charges that are counterbalanced, in this specific case, by protons. The protons in Al-β Zeolite (Zeolyst) were exchanged with tin cations, followed by calcinations.

Sn-β (Haldor Topsøe, A/S, Denmark): Presents similar structure to Al-β Zeolite, but contains structural Sn atoms instead of aluminum. Tin is tetrahedrally coordinated to the zeolite structure, but differently from aluminum, does not generated structural charges.

Suitability of Biomass-Derived Solvents:

Biphasic Reactors Using γ-Lactones as Extracting Layer and Homogeneous Catalysts:

Biphasic dehydration reactions were carried out in 10 mL thick-walled glass reactors heated in an oil bath at 170° C. Preparation of the aqueous layer comprised using solutions containing 5 mmol $L^{-1}$ $AlCl_3$ and adjusting their pH to 2.5 with HCl. The pH-adjusted solutions were saturated with NaCl, and cellulose or monosaccharide was added to obtain a 5 wt. % aqueous feed. In a typical experiment, 1.5 g of the aqueous feed and 3.0 g of γ-lactone were added to the reactor. The reactor was placed in the oil bath at 170° C. and stirred at 1000 rpm. Reactors were removed from the oil bath at specific reaction times and cooled in an ice-water bath.

In biphasic reactors using GVL as organic extracting layer, glucose and fructose can be converted to HMF in high selectivity.

Systems using GHL and GOL as an organic extracting layer produce HMF with selectivities comparable to that observed for GVL.

The system using GUL is less selective in the formation of HMF.

To evaluate using γ-lactones and THF as biomass-derived solvents for conversion of biomass, cellulose or C6 monossaccharides into HMF, a biphasic system was employed. See FIG. 4. In the biphasic reaction, substrates reaction takes place in the aqueous layer 9, followed by the extraction of HMF into the organic layer 10, where it is protected from catalysts, thus minimizing side reactions. The aqueous layer 9 must be saturated with NaCl to diminish the solubility of both the organic solvent and HMF, improving the efficiency of the organic extracting layer. As shown in FIG. 4, aluminium chloride was used as isomerization catalyst, and HCl was used as the dehydration catalyst. The upper organic layer, 10, comprised lactones (GVL, GHL, GOL, and GUL) derived from biomass.

TABLE 2

Conversion of cellulose, glucose or fructose to HMF in a biphasic system with γ-lactones, THF and SBP as the extracting organic layer.†

| Feed | Organic Layer | Time/min | Conv./% | Selec./% | % HMF in Org Layer | % HCl in Aq. Layer |
|---|---|---|---|---|---|---|
| Fructose | GVL | 20 | 94 | 84 | 94 | 30 |
| Glucose | GVL | 40 | 88 | 70 | 94 | 30 |
| Cellulose | GVL | 360 | 100 | 34 | 94 | 30 |
| Glucose | GHL | 40 | 88 | 65 | 92 | 20 |
| Glucose | GOL | 40 | 89 | 65 | 92 | 10 |
| Glucose | GUL | 40 | 92 | 54 | 83 | 0 |
| Glucose | THF [Ref 6] | — | 80 | 71 | 93 | 30 |
| Glucose | SBP [Ref 6] | 40 | 91 | 68 | 97 | 0 |

†Reaction conditions: 1.5 g of aqueous feed (5 wt % cellulose, glucose, or fructose, 5.0 mmol L⁻¹ AlCl₃ and 3.17 mmol L⁻¹ HCl); 3.0 g of organic solvent; T = 170° C.

As seen in the results presented in Table 2, the selectivity for conversion of glucose to HMF using the γ-lactones in a biphasic system (with the exception of GUL) are comparable with systems using THF and SBP as the extracting solvent. (See the final entry of Table 2). However, the γ-lactones extract a portion of the HCl from the aqueous layer. This does not render the process inoperable, but can impact HMF separation or upgrading. It also tends to increase process cost because the aqueous layer has to be re-acidified and the organic layer has to be neutralized. For example, the molar ratio of "HMF formed"-to-"HCl lost" is approximately 200 when using THF and GVL as the extracting solvents.

HCl Balance:

As mentioned before, one important aspect in the biphasic reactors is the extraction of the homogeneous catalysts by the organic layer. By titration of aqueous and organic layers, it was found that GVL and GHL can extract, respectively 30 and 20% of the HCl from the aqueous layer. Aqueous layers were directly titrated with a 0.01 mol L-1 sodium hydroxide solution using phenolphthalein as indicator. Organic layers were contacted with water to extract the HCl before titration.

Recycle of the System Using GHL as Organic Extracting Layer:

Experimental: For recycle experiments, an aqueous solution with 5 mM AlCl₃ was first prepared and adjusted to a pH of 2.5 with HCl. This mixture was saturated with NaCl, glucose was added to reach 5 wt %, and 1.5 g of the aqueous feed was added to a 10 mL thick-walled glass reactor containing 3.0 g of GHL. The reactor was heated in an oil bath to 443 K with stirring at 1000 rpm for 40 min. Upon completion of the reaction, reactors were cooled. The organic layer was extracted and glucose added to the remaining aqueous layer to obtain a 5 wt % glucose mixture. Fresh GHL was added to the reactor, and the reaction was carried out for consecutive runs, as described above.

TABLE 3

Conversion and selectivity for production of HMF from glucose in consecutive runs using GHL as extracting organic layer.ᵃ

| Run | Feed | Lactone | Time/min | Conversion/% | Selectivity/% |
|---|---|---|---|---|---|
| 1 | Glucose | GHL | 40 | 88 | 65 |
| 2 | Glucose | GHL | 40 | 85 | 68 |
|   | Glucose | GHL | 50 | 90 | 67 |
| 3 | Glucose | GHL | 40 | 66 | 66 |
|   | Glucose | GHL | 60 | 89 | 67 |
| 4 | Glucose | GHL | 40 | 65 | 68 |
|   | Glucose | GHL | 50 | 88 | 67 |

ᵃReaction conditions: 1.5 g of aqueous feed (5 wt % glucose, 5 mM AlCl₃ at pH to 2.5), 3.0 g of lactone; Temperature 443 K.

As observed in Table 3, for reusing the aqueous layer, it is necessary to increase the reaction time by 10 min after each reuse. This is a consequence of the extraction of a portion of the catalyst from the aqueous to the organic layer.

Monophasic Reactors Using Lactones, Hydrofurans or Hydropyrans with 10% of Water and Homogeneous Catalysts:

Of the solvents listed in Table 2, THF, GVL, and GHL can form a monophasic mixture with water. THF and GVL are miscible in water, while GHL can dissolve 7-10 wt % of water. The use of monophasic solvent systems alleviates potential mixing inefficiencies that may be encountered when scaling up biphasic systems.

Accordingly, the next set of reactions explored was the production of HMF from biopmass, cellulose or C6-sugar in a monophasic solvent system comprising of GVL, GHL, and/or THF with 10 wt % water using AlCl₃ and HCl as catalysts. (These reactions are depicted schematically in FIGS. 6-8.) As shown in Table 4, the results obtained in these monophasic systems are similar to those shown in Table 1.

TABLE 4

Conversion of cellulose, glucose, or fructose to HMF in a monophasic system with THF or γ-lactones and 10 wt. % water.†

| Feed | Organic Solvent | Time/min | Conversion/% | Selectivity/% |
|---|---|---|---|---|
| Glucose | GVL | 20 | 89 | 66 |
| Cellulose | GVL | 130 | 100 | 31 |
| Glucose | GHL | 20 | 90 | 65 |
| Glucose | THF | 20 | 90 | 56 |

†Reaction conditions: 1.5 g of organic solvent:water (9:1); feed = 2 wt % cellulose or glucose, 5.0 mmol L⁻¹ AlCl₃, and 3.17 mmol L⁻¹ HCl; T = 170° C.

Monophasic Reactors Using Lactones, Hydrofurans or Hydropyrans with 20% of Water and Homogeneous Catalysts:

Experimental:

In 10 mL thick-walled glass reactors were added 0.294 g of a 25 mM AlCl₃ aqueous solution with pH adjusted to 1.8 with HCl, 1.176 g of organic solvents and 0.03 g of cellulose or monosaccharide. The final concentrations were 2 wt % of cellulose or monosaccharide; 5 mM of AlCl₃; 3.2 mM of HCl. The weight ratio water:organic solvent is 1:4. The reactor was placed in the oil bath at 170° C. and stirred at 700 rpm. Reactors were removed from the oil bath at specific reaction times and cooled in an ice-water bath.

TABLE 5

Conversion of cellulose, glucose or fructose to HMF in a monophasic reactor with using lactones or THF and water in a ratio 4:1.[a]

| Feed | Solvent | Time/min | Conversion/% | Selectivity/% |
| --- | --- | --- | --- | --- |
| Fructose | GVL | 9 | 90 | 81 |
| Glucose | GVL | 20 | 89 | 66 |
| Cellulose | GVL | 130 | 100 | 31 |
| Glucose | THF | 20 | 90 | 56 |

[a]Reaction conditions: 1.5 g of feed (5 wt % cellulose, glucose or fructose, 5 mM AlCl$_3$ at pH to 2.5; water:organic solvent ratio of 1:4); Temperature 443 K.

In the monophasic reactors with a GVL:water weight ratio of 4:1, the selectivities for HMF obtained from cellulose, glucose or fructose are similar to those observed in the biphasic reactor.

The system using THF presents performance inferior to that using GVL.

In these monophasic systems, the homogeneous catalysts can be substituted for heterogenous catalysts.

An advantage of using monophasic systems (as contrasted to a biphasic systems) is that the addition of salt is not necessary (as it is to achieve a biphasic system with these same lactone solvents). This allows for replacing the homogeneous catalysts used for glucose isomerization and fructose dehydration with solid acid catalysts.

Heterogeneous Isomerization Catalysts:

To establish the most appropriate heterogeneous isomerization catalyst for glucose isomerization, a leaching test was performed for Sn-β (Si:Sn=400), Sn-SBA-15 (Si:Sn=40) and hydrotalcite. For this test, 0.1 g of catalyst was stirred in a mixture GVL:H$_2$O (9:1) for 30 min at 130° C. The catalyst was removed by filtering, and glucose was added to the solvent to make a 2 wt. % sugar solution. The mixture was stirred for 30 min at 130° C. Conversion of glucose was only observed in the solution contacted with hydrotalcite, indicating leaching.

The solid Brønsted acid catalyst used in the Examples of the monophasic reactor systems was Amberlyst 70 (Amb-70), a sulfonic acid-functionalized catalyst. Other solid acid catalyst may also be used in the process, such as zeolites (mordenite, ZSM-5, Z-Y, USY and Z-β), cubic and amorphous zirconium phosphate, titanium oxide, niobium oxide, phosphated niobic acid, etc. A previous study showed low deactivation of Amb-70 in the dehydration of fructose at 130° C. in a flow reactor system using THF:H$_2$O (4:1) as solvent. [10]

Effect of Water:

Because water is produced during glucose conversion to HMF, and the presence of water increases the solubility of glucose, the effect of water concentration was studied in the conversion of glucose to HMF using GVL as the solvent and Amb-70 and Sn-SBA-15 as catalysts. Although water is known to promote side reactions in the dehydration of sugars, [14] it can be seen in the unexpected results from FIG. 12 that water is beneficial in low concentrations, roughly less than about 20% and preferably between about 2% and about 15%, most preferably between about 2% and about 12% water. At similar conversion (~70%), the system with mass ratio GVL:H$_2$O (9:1) showed higher HMF selectivity than those with a GVL:H$_2$O ratio of 4:1 or pure GVL.

Table 6 shows the results for conversion of fructose and glucose to HMF using Amb-70 or a combination of Amb-70 and Sn-based catalysts (Sn-β or Sn-SBA-15) in GVL, GHL or THF containing 10 wt % water. These experiments were carried out for different catalysts and solvents at similar conversions (~90%). It can be seen that HMF was obtained from fructose using Amb-70 with selectivities between 80 and 85%. Direct dehydration of glucose using Amb-70 led to selectivities lower than 35%, in agreement with early reports showing that direct dehydration of glucose with mineral acids leads to low selectivity to HMF. [6, 30] The combination of a Sn-based catalyst and Amb-70 leads to significant improvement in the selectivity to HMF from glucose. Systems using Sn-β show at least 9% higher selectivity than those using Sn-SBA-15. Using Sn-β/Amb-70 for the conversion of glucose, selectivities of 64, 59 and 70% were obtained, respectively, using GVL, GHL and THF as the solvent.

Monophasic Reactors Using Lactones, Hydrofurans or Hydropyrans with 10% of Water and Heterogeneous Catalysts:

Experimental:

In 10 mL thick-walled glass reactors were added 0.03 g of monosaccharide, 0.147 g of water, 1.323 g of organic solvent and the appropriate amount of solid catalyst. The final solution contains 2 wt % of monosaccharide and a weight ratio water:organic solvent of 1:9. The reactor was placed in the oil bath at 403 K and stirred at 700 rpm. Reactors were removed from the oil bath at specific reaction times and cooled in an ice-water bath.

Table 6 shows the results for conversion of fructose and glucose to HMF using Amb-70 or a combination of Amb-70 and Sn-based catalysts (Sn-β or Sn-SBA-15) in GVL, GHL or THF containing 10 wt. % water. These experiments were carried out using different catalysts and solvents at similar conversions (~90%). It can be seen that HMF was obtained from fructose using Amb-70 with selectivities between 80 and 85%. On the other hand, direct dehydration of glucose using Amb-70 led to selectivities lower than 35%, in agreement with early reports showing that direct dehydration of glucose with mineral acids leads to low selectivity to HMF. The combination of a Sn-based catalyst and Amb-70 leads to significant improvement in the selectivity to HMF from glucose. Systems using Sn-β show at least 9% higher selectivity than those using Sn-SBA-15. In this respect, Taarning and co-workers have shown that Sn-β displays higher Lewis acid strength than Sn-SBA-15 which gives it significantly higher catalytic activity. Using Sn-β/Amb-70 for the conversion of glucose, selectivities of 64, 59 and 70% were obtained, respectively, using GVL, GHL and THF as the solvent.

Because methyltetrahydrofuran (MTHF) can be produced directly from biomass-derived furfural or GVL, the use of this solvent was also explored for conversion of glucose to HMF. MTHF is not miscible with water, and the conversion of glucose in a mixture of MTHF and water (9:1 ratio) is biphasic. The selectivity obtained for this system at 90% glucose conversion was 60%, which is comparable to reaction in GHL. To obtain a monophasic solvent system, half of the MTHF was substituted by THF, and the solvent system consisting of THF:MTHF (1:1) and 10 wt. % water produced a selectivity of 66% for HMF formation from glucose, which is comparable to that obtained in GVL.

TABLE 6

Conversion of glucose or fructose to HMF in a monophasic system using γ-lactones, THF or MTHF with water in a ratio (9:1).[a]

| Feed | Solvent | Lewis Acid | Time/min | Conv./% | Selec./% |
|---|---|---|---|---|---|
| Fructose[b] | GVL | — | 9 | 89 | 80 |
| Glucose[c] | GVL | — | 30 | 92 | 32 |
| Glucose[d] | GVL | Sn-β | 20 | 92 | 64 |
| Glucose[e] | GVL | Sn-SBA-15 | 15 | 90 | 51 |
| Fructose[b] | GHL | — | 10 | 91 | 81 |
| Glucose[c] | GHL | — | 30 | 85 | 30 |
| Glucose[d] | GHL | Sn-β | 20 | 93 | 59 |
| Glucose[e] | GHL | Sn-SBA-15 | 15 | 90 | 50 |
| Fructose[b] | THF | — | 10 | 91 | 85 |
| Glucose[c] | THF | — | 50 | 90 | 25 |
| Glucose[d] | THF | Sn-β | 30 | 90 | 70 |
| Glucose[e] | THF | Sn-SBA-15 | 20 | 90 | 40 |
| Glucose[c] | MTHF | — | 70 | 90 | 17 |
| Glucose[d] | MTHF | Sn-β | 50 | 89 | 60 |
| Glucose[c] | MTHF:THF[f] | — | 60 | 85 | 26 |
| Glucose[d] | MTHF:THF[f] | Sn-β | 40 | 91 | 66 |

[a]Reaction conditions: 1.5 g of feed (2 wt. % glucose or fructose, organic:water ratio (9:1)); Temperature 130° C.
[b]Catalysts: 0.05 g Amb-70;
[c]Catalysts: 0.1 g Amb-70;
[d]Catalysts: 0.05 g of Sn-β and 0.05 g Amb-70;
[e]Catalysts: 0.05 g of Sn-SBA-15 and 0.05 g Amb-70;
[f]THF:MTHF weight ratio (1:1);

FIGS. 13A to 13E show the conversion of glucose to fructose and HMF as a function of time in the presence of Amb-70 and Sn-β for GVL (FIG. 13A), GHL (FIG. 13B), THF (FIG. 13C), MTHF (FIG. 13D), and THF:MTHF (FIG. 13E). (Each of the stated solvents contained 10 wt % water. For all reactions: 2 wt % glucose; 0.05 g Sn-β; 0.05 g Amb-70; T=130° C.

In glucose conversion (FIGS. 13A-13E), the product observed initially is fructose, and formation of HMF begins at approximately 5 min of reaction time. Comparing the extent of fructose formation in the different solvents, it can be concluded that the effectiveness of glucose isomerization controls the HMF selectivity (see Table 6), i.e., THF>THF:MTHF=GVL>MTHF=GHL. Diminishing the mass ratio Amb-70/Sn-β in an attempt to increase the relative rate of glucose isomerization in GVL did not lead to any improvement in HMF selectivity. The results are shown in FIG. 14, which is a histogram showing % HMF yield as a function of Amb-70/Sn-β weight ratio. Thus, in addition to functioning as a catalyst for glucose isomerization, Sn-β also appears to catalyse fructose degradation to unidentified products. After HMF has been formed, it can undergo further reaction to form equimolar amounts of levulinic (LA) and formic acid (FA), as observed in FIGS. 13A-13E, generated from HMF hydrolysis (HMF=LA+FA). The carbon balances in the reactions carried out using GVL (FIG. 13A), GHL (FIG. 13B) and THF (FIG. 13C) were, respectively, 80, 65 and 85%. Common degradation products, such as humins, formed by the cross-polymerization of glucose and HMF [32] were not quantified.

More examples of monophasic reactors using lactones, hydrofurans or hydropyrans with 10% of water and heterogeneous catalysts:

TABLE 7

Conversion of glucose or fructose to HMF in a monophasic reactor with using lactones or THF and water in a ratio 9:1.

| Feed | Solvent | Lewis Acid (amount) | Brønsted acids (amount) | Time/min | Conv./% | Selec./% |
|---|---|---|---|---|---|---|
| Fructose | GVL | — | Amberlyst-70 (0.1 g) | 9 | 89 | 75 |
| Glucose | GVL | — | Amberlyst-70 (0.1 g) | 8 | 90 | 28 |
| Glucose | GVL | Sn-SBA-15 (0.05 g) | Amberlyst-70 (0.05 g) | 15 | 90 | 51 |
| Glucose | GVL | SnO$_2$/Al-β (0.05 g) | Amberlyst-70 (0.05 g) | 15 | 89 | 55 |
| Glucose | GVL | Sn-β (0.05 g) | Amberlyst-70 (0.1 g) | 15 | 89 | 62 |
| Glucose | THF | Sn-SBA-15 (0.1 g) | Amberlyst-70 (0.1 g) | 60 | 90 | 40 |
| Fructose | GHL | — | Amberlyst-70 (0.05 g) | 10 | 91 | 81 |
| Glucose | GHL | SnO$_2$/Al-β (0.05 g) | Amberlyst-70 (0.05 g) | 15 | 90 | 50 |
| Fructose | GOL | — | Amberlyst-70 (0.05 g) | 10 | 95 | 64 |
| Glucose | GOL | SnO$_2$/Al-β (0.05 g) | Amberlyst-70 (0.05 g) | 30 | 88 | 39 |

[a] Reaction conditions: 1.5 g of feed (5 wt % cellulose, glucose or fructose, water:organic solvent ratio of 1:9); Temperature 403 K.

GVL and GHL have shown to be the best solvents for the conversion of glucose and fructose to HMF. Using SnO$_2$-Al-β, selectivities around 50% were obtained at approximately 90% glucose conversion.

Comparing different isomerization catalysts for the system using GVL, it was found that, Sn-SBA-15 and SnO$_2$-Al-β have similar results, while Sn-β has a performance slightly superior.

Purifying, Concentrating, Isolating HMF from the Product Mix:

Because HMF is both a final product and a platform chemical to make downstream products, it is important to have efficient methods to separate HMF from the reaction medium or to integrate the production of HMF with subsequent upgrading reactions, thereby decreasing the cost of the final product. GVL and GHL have high boiling points that are similar to HMF; therefore, the separation of HMF from these solvents by distillation requires the use of low pressures and could lead to degradation of HMF. While these issues do not pose technological issues, the do raise economic issues that could impact the profitability of the process.

Extraction of HMF from GVL or GHL to Water:

As mentioned above, HMF can be removed from THF by distillation, and it can thus be used directly in the oxidation reaction. Removal of HMF from the less volatile γ-lactones solvents can be achieved by contacting these solutions containing HMF with water and cyclopentane (CP) in different proportions, as shown in Table 8. Similar results can be obtained with methylcyclopentane and any other alkane miscible with the lactones.

TABLE 8

Extraction of HMF from GVL and GHL to water using CP.

| Lactone | Extraction | CP/g | % HMF in water | % Lactone in water. |
|---|---|---|---|---|
| GVL | 1[a] | 20 | 90 | 43 |
|  | 2 | 20 | 80[b] | 5.00 |
|  | 3 | 20 | 97[b] | 1.80 |
|  | 4 | 20 | 99[b] | 0.5 |

TABLE 8-continued

Extraction of HMF from GVL and GHL to water using CP.

| Lactone | Extraction | CP/g | % HMF in water | % Lactone in water. |
|---|---|---|---|---|
| GHL | 1[a] | 16 | 80 | 5.00 |
| | 2 | 6 | 100[b] | 1.30 |
| | 3 | 6 | 100[b] | 0.35 |
| | 2 | 12 | 100[b] | 0.80 |

[a]For the first extraction, one part of a HMF solution in lactone was contacted with one part of water and the amount of CP specified in the table. The aqueous phase was separated from the biphasic mixture for subsequent extractions with CP.
[b]Based on the HMF remained in the aqueous layer on the previous extraction.

Contacting one (1) part of a solution containing HMF in GHL with one (1) part of water and 16 parts of CP, leads to an aqueous layer containing of 80 wt. % of the initial HMF and 5 wt. % of the initial GHL. Contacting the resultant aqueous layer twice with 6 parts of CP decreases the GHL concentration to 0.35 wt. % of the initial value, while retaining all of the HMF in the aqueous layer. The HMF: GHL molar ratio in the final aqueous layer is equal to 2.51. GVL is more soluble in water than GHL; therefore, extraction of HMF from GVL requires several consecutive extractions with CP to yield an aqueous solution with 80 wt. % of the initial HMF amount and 0.5 wt. % of the initial amount of GVL. The HMF:GVL molar ratio in the final aqueous layer is equal to 1.52. The boiling point of CP (50° C.) is much lower than GVL (207° C.) and GHL (219° C.), hence it can be separated easily from the lactone by distillation. More Examples of Extraction of HMF from GVL or GHL to Water:

In the examples described in Table 9, the catalysts can be separated from the reaction medium by filtration. HMF cannot be separated from the solvents by distillation, due to their high boiling point. An alternative is the extraction of HMF to aqueous layer as described for SBP in ref [6].

The high miscibility of GVL with water makes the extraction of HMF complicated. A mixture of GVL containing 1 wt % of HMF with water was contacted with different solvents in order to selectively remove the GVL from the aqueous layers, maintaining the HMF in the aqueous phase (Table 9).

TABLE 9

Extraction of HMF to water from GVL

| $H_2O$/g | 1% HMF in GVL/g | Solvent 1 (amount) | Solvent 2 (amount) | HMF/ Aqueous layer | GVL/ Aqueous layer | GVL/ HMF (g/g) |
|---|---|---|---|---|---|---|
| 2 | 1 | GUL (1 g) | — | 49% | 29% | 59 |
| 2 | 1 | GUL (1 g) | Hexane (2 g) | 67% | 33% | 48 |
| 2 | 1 | GUL (1 g) | Toluene (2 g) | 44% | 15% | 36 |
| 2 | 1 | GUL (1 g) | Hexane (4 g) | 84% | 35% | 42 |
| 2 | 1 | SBP (1 g) | Hexane (3 g) | 57% | 16% | 28 |
| 2 | 1 | SBP (1 g) | Toluene (3 g) | 38% | 7% | 18 |
| 2 | 1 | SBP (1 g) | Hexane (6 g) | 72% | 18% | 25 |

The best solvent systems to extract HMF from aqueous layer were GUL:hexane (1:4) and SBP/hexane (1:6).

Using GUL:hexane (1:4), 84% of HMF and 35% of GVL were present in the aqueous layer.

Using SBP/hexane (1:6), 72% of HMF and 18% of GVL were present in the aqueous layer.

GHL has a low solubility in water, hence an extraction of HMF to water is similar to that used for SBP in ref [6]. In this case, however, hexane cannot be used, since it is not miscible with GHL. Methylcyclopentane showed a good miscibility with GHL while it does not dissolve HMF. Therefore, GHL containing 1 wt % HMF was contacted with water and methylcyclopentane (Table 10).

TABLE 10

Extraction of HMF to water from GHL

| $H_2O$/g | 1% HMF in GHL/g | Methyl-cyclpentane/g | HMF/ Aqueous layer | GHL/ Aqueous layer | GHL/HMF (g/g) |
|---|---|---|---|---|---|
| 2 | 1 | — | 46% | 24% | 50 |
| 2 | 1 | 2 | 63% | 18% | 28 |
| 2 | 1 | 4 | 75% | 18% | 23 |
| 2 | 1 | 8 | 86% | 17% | 19 |
| 2 | 1 | 16 | 88% | 13% | 14 |
| 1 | 1 | 4 | 73% | 9% | 12 |
| 1 | 1 | 8 | 78% | 7% | 9 |

HMF can be extracted from GHL to water when the organic solvent is contacted with methylcyclopentane.

A fraction of GHL was found on the aqueous layer, however in much lower respect to GVL.

In the best condition, the weight ratio GHL/HMF in the aqueous layer is as low as 9, while 25 for GVL/HMF.

Metylcyclopentane has a low boiling point (345 K) and can be easily separated from GHL by distillation.

Production of 2,5-furandicarboxylic acid (FDCA)

One of the most attractive compounds that can be produced from HMF is 2,5-furandicarboxylic acid (FDCA). FDCA can be produced by oxidation of HMF with an oxidizing agent, such as, molecular oxygen in an aqueous alkaline solution using, for example, supported gold, platinum or palladium catalysts. [34-36] A great many other oxidation catalysts can also be used. FDCA is a monomer that can be used to produce polymers similar to polyethylene terephthalate (PET). PET has a growing market, with more than 49 million tons produced in 2009.[37] For this reason, FDCA has been rated as a top twelve value added chemical by the U.S. Department of Energy.[38] For the production of FDCA, HMF has to be separated to avoid oxidation of the organic solvent.

Aqueous solutions of HMF and γ-lactones (that could be produced by the method outlined above using CP) were used as feed solutions for studies of HMF oxidation under the reaction conditions proposed by Davis et al.[35] i.e., aqueous solution containing 0.1 mol $L^{-1}$ HMF, 2 mol $L^{-1}$ NaOH, 2000 kPa oxygen, 1 wt. % $Au/TiO_2$ (HMF:Au=100) at 22° C. Using an aqueous solution of HMF with up to 0.5% of GVL or GHL, yields of 80% for FDCA and 20% for 2-hydroxymethylfurancarboxylic acid (HFCA) were observed, in accordance with previous literature in the absence of lactones. [35] When the reaction was carried out in the presence of larger amounts of lactones (i.e., 5%), yields of 56% for FDCA and 44% for HFCA were observed, and 35% of the γ-lactone was converted to levulinic acid (from GVL) or 4-oxohexanoic acid (from GHL). Separation of FDCA was achieved by decreasing the pH of the reaction mixture to a value of 1, leading to precipitation of FDCA, while HFCA and salt remained in solution.

Oxidation of HMF in Presence of Lactones:

HMF can be oxidized into FDCA in presence of the lactones or after being extracted into water using continuous reactor or batch reactors.

Any catalysts able to oxidize HMF can be used in the process. For example, Pt/C and Au/C were placed in a stainless steel tubular reactor (6.35 mm OD) and held between two end plugs of silica granules and quartz wool. The catalyst was reduced in-situ for 3 h at 3000° C. (1° C. min$^{-1}$) before use. The feed was introduced into the reactor using an HPLC pump (Lab Alliance-brand Series I; Scientific System, Inc., State College, Pa., USA). Air or $O_2$ was flow during the reaction (25 cm$^3$(STP)/min) was controlled by a mass flow controller (Brooks Instrument, 5850S; Brooks Instrument, Inc., Hatfield, Pa., USA). The tubular reactor was fitted inside an aluminum block and placed within an insulated furnace (Applied Test Systems, Butler, Pa., USA). Bed temperature was monitored at the reactor wall using a Type K thermocouple (Omega Engineering, Inc., Stamford, Conn., USA) and controlled using a 16A series programmable temperature controller (Love Controls, Inc., Michigan City, Ind., USA). Reactor pressure (1 to 35 bar) was controlled using a back pressure regulator (model BP-60; GO Regulator, Inc, Spartanburg, S.C., USA). The reactor effluent flowed into a vapor-liquid separator wherein the liquid product was collected.

For batch reactions, a 50 mL Parr Instruments Hastelloy C-276 batch reactor (Parr Instrument Company, Moline, Ill., USA), equipped with a variable speed magnetic stirrer, was loaded with reduced and passivated catalyst. The system was purged with helium, pressurized with Air or $O_2$ to the desired pressure and heated to the reaction temperature using a heating mantle. At the end of the reaction, the reactor was cooled and weighed. A sample was taken from the reactor to be analyzed before and at the end of the reaction.

HMF Oxidation in Presence of GVL:

250 mg of 10 wt % Pt/C were loaded in a flow reactor and a solution of 79 wt % GVL, 20 wt % water and 1 wt % HMF. Reaction was conducted at a temperature of 100° C. and pressure 13.6 bar of Air. The results are summarized in Table 11.

TABLE 11

Oxidation HMF to FDCA in 4:1 GVL:H$_2$O.$^a$

| Feed flow rate (ml/min) | FDCA yield (%) |
|---|---|
| 0.05 | 45 |
| 0.01 | 62 |

$^a$100° C., 13.6 bar Air. 250 mg 10 wt % Pt/C

Oxidation of HMF to FDCA in Presence GVL Using Molecular Oxygen:

HMF was oxidized to FDCA over a supported gold catalyst. The reaction was carried out in the absence of a base. Molecular oxygen was used as the oxidant. The general reaction conditions were:

22 grams of 0.5 wt % HMF in GVL/H$_2$O (about 80/20 wt %) solution.

0.5 grams of 2 wt % Au/HT.

100 to 700 psi O$_2$ pressure.

Reaction conducted at 50 to 95° C. for 4 to 72 hours

The following is an exemplary run:

0.15 grams of HMF was added to 30 grams of 80/20 GVL/H$_2$O mixture to obtain a 0.5 wt % HMF solution in GVL solvent. 22 grams of the above mixture was added to a Parr autoclave reactor along with 0.3-0.6 grams of 2 wt % supported gold catalyst. The reactor was purged with O$_2$ three times and was pressurized to 100-700 psi with O$_2$. HMF was oxidized at 95° C. for 12 hours. In a typical reaction HMF conversion was about 97% and FDCA selectivity was greater than 94% (Table 12).

TABLE 12

Composition of the feed and product mixture.

| | Concentration (wt %) | | |
|---|---|---|---|
| | | Product Mixture | |
| Component | Feed | Aqueous Phase* | Organic Phase* |
| Mass | 22 | 5.54 | 16.25 |
| HMF | 0.49 | 0 | 0.015 |
| FDCA | 0.00 | 2.101 | 0.063 |

*After the addition of toluene to the product mixture.

The catalyst was filtered and a biphasic reaction mixture was obtained. The product mixture was biphasic even before the addition of organic solvent. However, a significant fraction (>32%) of FDCA was retained in the organic layer. Toluene was added to the reaction mixture to partition the remaining FDCA into the aqueous layer. The separation of these two phases was carried out using a separatory funnel, and the phases were then analyzed by HPLC for HMF and FDCA and other oxidation products. Excellent separation of GVL and FDCA was achieved with more than 90% FDCA recovered in the aqueous phase as shown in Table 12.

Before toluene was added to the reaction mixture, the organic phase had a mass of 18.26 g; HMF accounted for 0.030 wt % and FDCA accounted for 0.165 wt % of the organic phase. After toluene was added to the reaction mixture, the organic phase had a mass of 16.25 g; HMF accounted for 0.015 wt % and FDCA accounted for 0.063 wt % of the organic phase. Thus prior to adding toluene, 28.5% of the FDCA formed was retained in the organic phase. After adding toluene, only 8.1% of the FDCA formed was retained in the organic phase.

Similarly, before toluene was added to the reaction mixture, the aqueous phase had a mass of 3.43 g; HMF accounted for 0.00 wt % and FDCA accounted for 2.20 wt % of the aqueous phase. After toluene was added to the reaction mixture, the aqueous phase had a mass of 5.54 g; with HMF accounted for 0.00 wt % and FDCA accounted for 2.10 wt % of the aqueous phase.

REFERENCES CITED

The following documents are incorporated herein by reference.

1. J. J. Bozell and G. R. Petersen, *Green Chemistry*, 2010, 12, 539-554.
2. M. J. Antal Jr, W. S. L. Mok and G. N. Richards, *Carbohydrate Research*, 1990, 199, 91-109.
3. J. Guan, Q. A. Cao, X. C. Guo and X. D. Mu, *Comput Theon Chem*, 2011, 963, 453-462.
4. A. S. Amarasekara, L. D. Williams and C. C. Ebede, *Carbohydrate Research*, 2008, 343, 3021-3024.
5. J. F. Robyt, *Essentials of carbohydrate chemistry*, Springer Pub. Co., New York, 1998.
6. Y. J. Pagan-Torres, T. F. Wang, J. M. R. Gallo, B. H. Shanks and J. A. Dumesic, *Acs Catal*, 2012, 2, 930-934.
7. C. Moreau, A. Finiels and L. Vanoye, *Journal of Molecular Catalysis A: Chemical*, 2006, 253, 165-169.

8. Y. Roman-Leshkov, J. N. Chheda and J. A. Dumesic, *Science*, 2006, 312, 1933-1937.
9. J. N. Chheda, Y. Roman-Leshkov and J. A. Dumesic, *Green Chemistry*, 2007, 9, 342-350.
10. A. J. Crisci, M. H. Tucker, M. Y. Lee, S. G. Jang, J. A. Dumesic and S. L. Scott, *Acs Catal*, 2011, 1, 719-728.
11. H. Zhao, J. E. Holladay, H. Brown and Z. C. Zhang, *Science*, 2007, 316, 1597-1600.
12. J. B. Binder and R. T. Raines, *Journal of the American Chemical Society*, 2009, 131, 1979-1985.
13. G. Yong, Y. Zhang and J. Y. Ying, *Angewandte Chemie International Edition*, 2008, 47, 9345-9348.
14. Y. Roman-Leshkov, C. J. Barrett, Z. Y. Liu and J. A. Dumesic, *Nature*, 2007, 447, 982-U985.
15. Y. Roman-Leshkov and J. Dumesic, *Topics in Catalysis*, 2009, 52, 297-303.
16. K.-i. Shimizu, R. Uozumi and A. Satsuma, *Catalysis Communications*, 2009, 10, 1849-1853.
17. Y. Zhang, K. Hidajat and A. K. Ray, *Biochemical Engineering Journal*, 2004, 21, 111-121.
18. H. B. Zhao, J. E. Holladay, H. Brown and Z. C. Zhang, *Science*, 2007, 316, 1597-1600.
19. M. E. Zakrzewska, E. Bogel-Lukasik and R. Bogel-Lukasik, *Chem Rev*, 2011, 111, 397-417.
20. R. L. Huang, W. Qi, R. X. Su and Z. M. He, *Chem Commun*, 2010, 46, 1115-1117.
21. D. M. Alonso, J. Q. Bond and J. A. Dumesic, *Green Chemistry*, 2010, 12, 1493-1513.
22. J. C. Serrano-Ruiz, R. Luque and A. Sepulveda-Escribano, *Chem Soc Rev*, 2011, 40, 5266-5281.
23. L. E. Manzer, *Appl Catal a-Gen*, 2004, 272, 249-256.
24. T. M. Ugurchieva, A. V. Lozanova, M. V. Zlokazov and V. V. Veselovsky, *Russ Chem B+*, 2008, 57, 657-659.
25. Y. Zhou, L. K. Woo and R. J. Angelici, *Applied Catalysis A: General*, 2007, 333, 238-244.
26. O. W. Cass, *Industrial & Engineering Chemistry*, 1948, 40, 216-219.
27. E. J. Garcia-Suarez, A. M. Balu, M. Tristany, A. B. Garcia, K. Philippot and R. Luque, *Green Chemistry*, 2012, 14, 1434-1439.
28. A. Takagaki, M. Ohara, S. Nishimura and K. Ebitani, *Chem Commun*, 2009, 6276-6278.
29. M. Moliner, Y. Roman-Leshkov and M. E. Davis, *P Natl Acad Sci USA*, 2010, 107, 6164-6168.
30. E. Nikolla, Y. Roman-Leshkov, M. Moliner and M. E. Davis, *Acs Catal*, 2011, 1, 408-410.
31. C. M. Osmundsen, M. S. Holm, S. Dahl and E. Taarning, *P Roy Soc a-Math Phy*, 2012, 468, 2000-2016.
32. H. M. Pilath, M. R. Nimlos, A. Mittal, M. E. Himmel and D. K. Johnson, *J Agr Food Chem*, 2010, 58, 6131-6140.
33. S. G. Wettstein, D. M. Alonso, Y. Chong and J. A. Dumesic, *Energy & Environmental Science*, 2012, 5, 8199-8203.
34. B. N. Zope, S. E. Davis and R. J. Davis, *Topics in Catalysis*, 2012, 55, 24-32.
35. S. E. Davis, B. N. Zope and R. J. Davis, *Green Chemistry*, 2012, 14, 143-147.
36. S. E. Davis, L. R. Houk, E. C. Tamargo, A. K. Datye and R. J. Davis, *Catal Today*, 2011, 160, 55-60.
37. In *Eurasian Chemical Market Inetrnational Magazine*, 2011, vol. 8, p. 56.
38. T. A. Werpy and G. Petersen, U.S. Department of Energy, 2004.
39. P. Shah, A. V. Ramaswamy, K. Lazar and V. Ramaswamy, *Micropor Mesopor Mat*, 2007, 100, 210-226.
40. Wyman, C. E., et al., *Coordinated development of leading biomass pretreatment technologies.* Bioresource Technology, 2005. 96(18): p. 1959-1966.
41. Alamillo, R., et al., *The selective hydrogenation of biomass-derived 5-hydroxymethylfurfural using heterogeneous catalysts.* Green Chemistry, 2012. 14(5): p. 1413-1419.
42. Tucker, M. H., *Selective Production of Value Added Chemicals From Fructose Using Heterogeneous Catalysis*, in *Chemical & Biological Engineering*. 2011, University of Wisconsin-Madison: Madison.
43. Dutta, S., et al., *Direct conversion of cellulose and lignocellulosic biomass into chemicals and biofuel with metal chloride catalysts.* Journal of Catalysis, 2012. 288: p. 8-15.
44. Yang, Y., C. W. Hu, and M. M. Abu-Omar, *Conversion of carbohydrates and lignocellulosic biomass into 5-hydroxymethylfurfural using AlCl3 center dot 6H(2)O catalyst in a biphasic solvent system.* Green Chemistry, 2012. 14(2): p. 509-513.

What is claimed is:

1. A process to produce furandicarboxylic acid (FDCA), the process comprising:
   (a) reacting a C6 sugar-containing reactant in a reaction solution comprising a first organic solvent selected from the group consisting of beta-, gamma-, and delta-lactones, hydrofurans, hydropyrans, and combinations thereof, in the presence of an acid catalyst for a time and under conditions wherein at least a portion of the C6 sugar present in the reactant is converted to 5-(hydroxymethyl)furfural (HMF); and
   (b) oxidizing at least a portion of the HMF from step (a) into FDCA with or separating the HMF or a fraction of HMF from the reaction solution.

2. The method of claim 1, wherein the first organic solvent is miscible with water.

3. The method of claim 1, wherein the first organic solvent can dissolve from 2 wt % to 25 wt % water.

4. The method of claim 1, wherein the first organic solvent is a combination of two or more solvents, wherein at least one of the solvents is miscible with water and at least one of the other solvents is not miscible with water.

5. The method of claim 1, wherein the acid catalyst is a solid acid catalyst selected from the group consisting of solid Brønsted acid catalysts, solid Lewis acid catalysts, and combinations thereof.

6. The method of claim 1, wherein the acid catalyst is a homogeneous acid catalyst selected from the group consisting of Lewis acid catalysts, Brønsted acid catalysts, and combinations thereof.

7. The method of claim 1, wherein in step (b), at least a portion of the HMF is oxidized into FDCA by contacting the HMF with an oxidizing catalyst in the presence of an oxidizing agent.

8. The method of claim 7, wherein the oxidizing catalyst is a metal containing catalyst and the oxidizing agent is molecular oxygen.

9. The method of claim 8, wherein the molecular oxygen is present at a pressure of from about 6.805 atm to about 68.05 atm.

10. The method of claim 8, wherein the metal-containing catalyst comprises a metal or a combination of metals selected from the group consisting of ruthenium, rhodium, palladium, silver, osmium, iridium, platinum, gold, mercury, rhenium, and copper.

11. The method of claim 8, wherein the metal-containing catalyst comprises a precious metal catalyst and a base metal catalyst.

12. The method of claim 11, wherein the molecular oxygen is present atr a pressure of rom about 6.805 atm to about 68.05 atm; and the metal-containing catalyst comprises a metal selected from the group consisting of ruthenium, rhodium, palladium, silver, osmium, iridium, platinum, gold, mercury, rhenium, and copper.

13. The method of claim 1, wherein step (b) is carried out in the absence of added base.

14. The method of claim 1, further comprising:
(c) extracting at least a portion of the FDCA by adding to the reaction solution of step (b) a second organic solvent selected from the group consisting of linear, branched or cyclic alkanes; linear, branched or cyclic alkenes; linear, branched or cyclic ketones; linear, branched or cyclic alcohols; aromatic hydrocarbons; phenol, and alkyl-substituted phenols.

15. The method of claim 1, further comprising:
(c) extracting at least a portion of the FDCA by adding to the reaction solution of step (b) a second organic solvent selected from the group consisting of saturated hydrocarbons, halo-substituted saturated hydrocarbons, aromatic hydrocarbons, and halo-substituted aromatic hydrocarbons.

16. The method of claim 1, further comprising:
(c) extracting at least a portion of the FDCA by adding to the reaction solution of step (b) a second organic solvent selected from the group consisting of benzene and toluene.

17. A process to produce furandicarboxylic acid (FDCA), the process comprising:
(a) reacting a C6 sugar-containing reactant in a reaction solution comprising a first organic solvent selected from the group consisting of beta-, gamma-, and delta-lactones, hydrofurans, hydropyrans, and combinations thereof, in the presence of a heterogenous acid catalyst for a time and under conditions wherein at least a portion of the C6 sugar present in the reactant is converted to 5-(hydroxymethyl)furfural (HMF);
(b) oxidizing at least a portion of the HMF from step (a) into FDCA without separating the HMF from the reaction solution; and
(c) extracting at least a portion of the FDCA by adding to the reaction solution of step (b) a second organic solvent which is an aprotic organic solvent having a dipole moment of about 1.0 D or less.

18. The method of claim 17, wherein the second organic solvent is selected from the group consisting saturated hydrocarbons, halo-substituted saturated hydrocarbons, aromatic hydrocarbons, and halo-substituted aromatic hydrocarbons.

19. The method of claim 17, wherein the second organic solvent is selected from the group consisting of benzene and toluene.

20. The method of claim 17, wherein in step (b) at least a portion of the HMF is oxidized into FDCA by contacting the HMF with an oxidizing catalyst in the presence of an oxidizing agent.

21. The method of claim 20, wherein the oxidizing catalyst is a metal containing catalyst and the oxidizing agent is molecular oxygen.

22. The method of claim 21, wherein the molecular oxygen is present at a pressure of from about 6.805 atm to about 68.05 atm.

23. The method of claim 20, wherein the catalyst comprises a metal or a combination of metals selected from the group consisting of ruthenium, rhodium, palladium, silver, osmium, iridium, platinum, gold, mercury, rhenium, and copper.

24. The method of claim 20, wherein the metal-containing catalyst comprises of a precious metal catalyst and a base metal catalyst.

25. The method of claim 24, wherein step (b) is carried out in the absence of added base.

* * * * *